(12) United States Patent
Wang et al.

(10) Patent No.: US 7,252,954 B2
(45) Date of Patent: Aug. 7, 2007

(54) SETS OF DIGITAL ANTIBODIES DIRECTED AGAINST SHORT EPITOPES, AND METHODS USING SAME

(75) Inventors: Jianfu Jeffrey Wang, Union City, CA (US); Weixing Helen Hu, Union City, CA (US)

(73) Assignee: Abmetrix, Inc., Union City, CA (US)

( * ) Notice: Subject to any disclaimer, the term of this patent is extended or adjusted under 35 U.S.C. 154(b) by 0 days.

(21) Appl. No.: 10/687,174

(22) Filed: Oct. 15, 2003

(65) Prior Publication Data

US 2004/0166106 A1 Aug. 26, 2004

Related U.S. Application Data

(60) Provisional application No. 60/496,124, filed on Aug. 18, 2003, provisional application No. 60/418,277, filed on Oct. 15, 2002.

(51) Int. Cl.
*G01N 33/50* (2006.01)

(52) U.S. Cl. .................. 435/7.1; 435/6; 435/287.2; 530/387.1; 530/387.2

(58) Field of Classification Search ................ 435/7.1, 435/6, 287.2; 530/387.1–387.2
See application file for complete search history.

(56) References Cited

U.S. PATENT DOCUMENTS

| | | | |
|---|---|---|---|
| 4,774,339 | A | 9/1988 | Haugland et al. |
| 5,384,263 | A * | 1/1995 | Kauvar .................. 436/518 |
| 5,538,897 | A | 7/1996 | Yates, III et al. |
| 6,274,323 | B1 | 8/2001 | Bruchez et al. |
| 6,365,418 | B1 | 4/2002 | Wagner et al. |
| 6,410,245 | B1 * | 6/2002 | Northrop et al. ............ 435/7.1 |
| 6,579,719 | B1 | 6/2003 | Hutchens et al. |
| 2003/0045694 | A1 * | 3/2003 | Chait et al. ................ 536/23.1 |
| 2004/0038319 | A1 | 2/2004 | Aebersold et al. |

OTHER PUBLICATIONS

Belov et al. Cancer Res. 2001 66: 4483.*
Geysen et al. J. Mol. Recognition 1988 vol. 1, p. 32.*

Afzalpurkar, A. et al. (1997). "Identification of Epitopes of Monoclonal Antibodies to Porcine Zona Pellucida 3β Glycoprotein, A Homologue of the Mouse/Human Sperm Receptor," *American Journal of Reproductive Immunology* 38:26-32.

Åkerblom, L. et al. (1990). "Neutralizing Cross-Reactive and Non-Neutralizing Monoclonal Antibodies to HIV-1 gp120," *AIDS* 4:953-960.

Demangel, C. et al. (2000). "Combining Phage Display and Molecular Modeling to Map the Epitope of a Neutralizing Antitoxin and Antibody," *Eur. J. Biochem* 267:2345-2353.

Hollborn, M. et al. (1999). "Epitope Mapping of a Monoclonal Antibody Directed Against the a-Subunit of Phosphofructokinase-1 From *Saccharomyces cerevisiae* By screening Phage Display Libraries," *Journal of Molecular Recognition* 12:33-37.

Malorny, B. et al (1998). "Sequence Diversity, Predicted Two-Dimensional Protein Structure, and Epitope Mapping of Neisserial Opa Proteins," *Journal of Bacteriology* 180(5):1323-1330.

Morelli, G. et al. (1997). "Clonal Descent and Microevolution of *Neisseria meningitidis* During 30 Years of Epidemic Spread," *Mol. Microbiol.* 25(6):1047-1064.

Nagasaki, H. et al. (1999). "Epitope Analysis of A Prostate-Specific Antigen (PSA) C-Terminal-Specific Monoclonal Antibody and New Aspects for the 2 Discrepancy Between Equimolar and Skewed PSA Assays," *Clin. Chem.* 45(4):486-496.

Zheng, X. et al. (1996). "Epitope Mapping of the Variable Repetitive Region Within the MB Antigen of Ureaplasma Urealyticum," *Clinical and Diagnostic Laboratory Immunology* 3(6):774-778.

U.S. Appl. No. 10/921,380, Urdea et al.

Saul, F. A. et al. (1996). "Crystallographic Studies of Antigen—Antibody Interactions," Chapter 2 In *Methods in Molecular Biology: Epitope Mapping Protocols.* G. E. Morris, ed., Humana Press: Totowa, New Jersey, vol. 66, pp. 11-23.

Michaud, G.A. et al. (2003). "Analyzing Antibody Specificity with Whole Proteome Microarrays," *Nature Biotechnology* 21(12):1509-1512.

* cited by examiner

*Primary Examiner*—Long V. Le
*Assistant Examiner*—Jacob Cheu
(74) *Attorney, Agent, or Firm*—Morrison & Foerster LLP

(57) ABSTRACT

The present invention relates generally to sets of digital antibodies directed against short epitopes, and use thereof in methods for protein analysis.

19 Claims, 4 Drawing Sheets

SETS OF DIGITAL ANTIBODIES DIRECTED AGAINST SHORT EPITOPES, AND METHODS USING SAME

CROSS-REFERENCE TO RELATED APPLICATIONS

This application claims the priority benefit of U.S. Provisional Patent Applications Ser. Nos. 60/418,277, filed Oct. 15, 2002, and 60/496,124, filed Aug. 18, 2003, the contents of both of which are incorporated by reference in their entirety.

FIELD OF INVENTION

The present invention relates generally to sets of digital antibodies directed against short epitopes, and use thereof in methods for protein analysis.

STATEMENT REGARDING FEDERALLY SPONSORED RESEARCH OR DEVELOPMENT

Not applicable.

BACKGROUND OF THE INVENTION

Proteomics involves the measurement of gene activity at the protein level. Today, the most common tool for proteomics purposes is the combination of two-dimensional gel electrophoresis coupled with mass spectrometry (2D-MS). This system has several limitations. First, the detection sensitivity and resolution of 2D electrophoresis is low. Second, use of mass spectrometric analysis dramatically increases the cost. Finally, 2D electrophoresis is time-consuming. A very well-equipped laboratory can only perform about 200 to 400 2D gels each week. Accordingly, there is a need for improved protein-analysis methods.

Detection and characterization of bacterial or viral infection is of crucial importance in the practice of clinical microbiology and in environmental testing, such as food safety and biohazard safety testing. Microorganisms are very diverse in terms of both phenotype and genotype, for instance, staphylococci consist of 32 species and 15 subspecies. Current diagnostic methods, however, are generally capable of detecting only a single microorganism or virus, necessitating the use of a number of specific tests in order to detect and characterize a microorganism or virus. Thus, there is a need for new methods for detection and characterization (including identification) of protein samples, including samples comprising or derived from bacteria and/or viruses.

Cancer can be classified based on tissue type and site of cancer. Each type of cancer can be further classified to different stages based on mostly tumor size and whether it has invaded other organ. For example, a prostate cancer may be classified into stages from T0 to T4 using current methods. In another example, cancers can also be classified to different grades based on, e.g., structural organization of a tumor, and/or the level of cell differentiation. However these morphological and/or histological classifications often do not correlate well with clinical treatment, and frequently fail to identify early stage cancer or pre-cancerous cells. Thus there is a need for new methods for detection and characterization (including identification) of protein samples comprising or derived from cancerous cells and/or tissues.

All references cited herein, including patent applications and publications, are incorporated by reference in their entirety.

SUMMARY OF THE INVENTION

The present invention provides sets of digital antibodies, and methods comprising use of digital antibodies.

Accordingly, in one aspect, the invention provides sets of digital antibodies, wherein the set comprises at least about 15 digital antibodies, wherein each digital antibody binds a different epitope, and wherein each digital antibody binds an epitope consisting of 3 consecutive amino acids, or 4 consecutive amino acids. In some embodiments, the set comprises at least about any of 20, 30, 40, 50, 60, 70, 80, 90, 100, 110, 125, 150, 175, 200, 300, 400, 500, 600, 700, 800, 900, 1000, or more antibodies. In some embodiments, the set comprises 100 digital antibodies that bind epitopes consisting of 3 consecutive amino acids. In other embodiments, the set further comprises 100 digital antibodies that bind epitopes consisting of 4 consecutive amino acids. In still other embodiments, the set further comprises 100 digital antibodies that bind epitopes consisting of 5 consecutive amino acids. In other embodiments, the set of digital antibodies comprises at least about 100, 200, 300, 400, 500, 600, 700, 800, 900, or 1000 digital antibodies, wherein each digital antibody binds a different epitope, and wherein each digital antibody binds an epitope consisting of 3 consecutive amino acids, 4 consecutive amino acids, or 5 consecutive amino acids. In still other embodiments, the set of digital antibodies comprises at least 1000 digital antibodies that bind epitopes consisting of 4 consecutive amino acids. In still other embodiments, the set further comprises at least 100 digital antibodies that bind epitopes consisting of 5 consecutive amino acids. In other embodiments, the set further comprises at least 100 digital antibodies that bind epitopes consisting of 3 consecutive amino acids. It is understood that "different epitopes" encompasses epitopes with overlapping amino acid sequences, as well as epitope with non-overlapping amino acid sequences.

In another aspect, the invention provides an array comprising any of the digital antibody sets described herein. Methods for generating arrays are well known in the art, and further described herein.

In another aspect, the invention provides methods for generating a protein binding profile said methods comprising (a) contacting a sample with any of the sets of digital antibodies described herein under conditions that permit binding; (b) optionally removing unbound protein (in some embodiments, removing protein that is not specifically bound); and (c) detecting binding of protein to antibodies, whereby a protein binding profile is generated.

In another aspect, the invention provides methods for generating a protein binding profile, said methods comprising detecting protein bound to a set of digital antibodies, whereby a protein binding profile is generated, wherein the protein bound to the set of digital antibodies is generated by a methods comprising (a) contacting a sample with any of the sets of digital antibodies described herein; and (b) optionally removing unbound protein.

In another aspect, the invention provides methods for generating a protein binding profile, said methods comprising (a) separating unbound protein from a set of digital antibodies contacted with a sample; and (b) detecting binding of protein to antibodies, whereby a protein binding profile is generated, wherein the unbound protein from a set of digital antibodies contacted with a sample is generated by a method comprising contacting a sample with any of the sets of digital antibodies described herein.

As is evident, one or more steps may be combined and/or performed sequentially (often in any order, as long as the requisite product(s) are able to be formed), and, as is evident, the invention includes various combinations of the steps described herein. It is also evident, and is described herein, that the invention encompasses methods in which the initial, or first, step is any of the steps described herein. Methods of the invention encompass embodiments in which later, "downstream" steps are an initial step.

In another aspect, the invention provides methods for generating a protein binding profile, said methods comprising (a) incubating a reaction mixture, said reaction mixture comprising: (i) any of the sets of digital antibodies described herein; and (ii) a sample; wherein the incubating is under condition permitting binding; (b) optionally separating unbound protein; and (c) detecting binding of protein to antibodies, whereby a protein binding profile is generated.

In another aspect, the invention provides methods for generating a protein binding profile, said methods comprising detecting binding of protein to a set of digital antibodies, whereby a protein binding profile is generated, wherein the protein bound to the set of digital antibodies is generated by a methods comprising incubating a reaction mixture, said reaction mixture comprising: (i) any of the sets of digital antibodies described herein; and (ii) a sample; wherein the incubating is under condition permitting binding; (b) optionally separating unbound protein.

As is evident to one skilled in the art, aspects that refer to combining and incubating the resultant mixture also encompasses method embodiments which comprise incubating the various mixtures (in various combinations and/or subcombinations) so that the desired products are formed.

In some embodiments, the methods of generating a protein binding profile further comprise a step of treating the sample with a protein cleaving agent, whereby polypeptide fragments are generated. The sample can treated with a protein cleaving agent prior to step (a) of contacting the sample with the set of digital antibodies under conditions that permit binding. The protein cleaving agent may be an enzyme (such as chymotrypsin or trypsin) or a chemical agent (such as cyanogen bromide).

It is understood that a protein binding profile includes information regarding absence of binding between a digital antibody and protein. It is further understood that a protein binding profile may be generated without the need to have prior knowledge of the identity of the protein being analyzed, and both known and unknown proteins may be detected. Thus, in some embodiments, the protein binding profile may be used to identify and/or detect a previously unknown agent, such as a novel pathogen.

Detection may be qualitative and/or quantitative. In some embodiments, binding of at least about 95%, at least about 90%, at least about 75%, at least about 50%, at least about 30% of antibodies in a set is detected. In some embodiments, binding of each antibody in a set is detected. In some embodiments, presence or absence and/or amount of bound labeled protein is detected. In other embodiments, labeled competitor polypeptide is detected, as further described herein. Generally, in embodiments involving use of competitor polypeptides, the methods further comprise contacting the set of digital antibodies with competitor polypeptides (in combination with the sample and/or sequentially with the sample).

In another aspect, the invention provides methods for generating libraries of protein binding profiles, comprising the steps of (a) contacting a sample with any of the sets of digital antibodies described herein under conditions that permit binding; (b) optionally removing unbound protein (in some embodiments, removing protein that is not specifically bound); (c) detecting binding of protein to antibodies, whereby a protein binding profile is generated; and (d) repeating steps (a) through (c) with at least two different samples.

In another aspect, the invention provides methods for generating libraries of protein binding profiles, comprising: compiling a set of two or more protein binding profiles, wherein the protein binding profiles are prepared according to any of the methods for generating protein binding profiles described herein.

In another aspect, the invention provides libraries of protein binding profiles, wherein the library is prepared using any of the methods described herein.

In some embodiments, the libraries may comprise at least about 5, 10, 15, 20, 25, 30, 35, 40, 45, 50, 75, 100, 150, 200, 300, 400, 500, 600, 700, 800, 900, or more (such as 1000, 2000, 3000, 4000 or more) binding profiles.

In another aspect, the invention provides methods using the protein binding profiles (including libraries of protein binding profiles) generated according to the methods of the invention. Thus, the invention provides methods for characterizing a test sample (such as a test sample suspected of comprising a sample of interest); methods for detecting presence or absence and/or identifying a test sample; methods for characterizing a cell, bacteria and/or virus; methods for identifying a test protein; methods for characterizing, detecting presence and/or absence and/or identifying a protein complex; and methods for screening, as further described herein. The invention further provides methods for detecting presence or absence and/or characterizing of a sample comprising or derived from a cell, such as a prokaryotic cell (such as a bacterium), an eukaryotic cell, a mammalian cell (including human, and non-human mammals, such as murine), a cancer or precancerous cell, or a microorganisms, such as a virus, as well as methods for detecting and/or diagnosing presence or absence of other disease and/or abnormality (such as type and/or stage of cancer, or identification of a precancerous cell), as further described herein.

In one aspect, the invention provides methods for characterizing a test sample (such as a test sample suspected of comprising a sample of interest), said methods comprising (a) contacting the test sample with any of the sets of digital antibodies described herein under conditions that permit binding; (b) optionally removing unbound protein; (c) detecting binding of protein to antibodies, whereby a protein binding profile is generated; and (d) comparing the protein binding profile of the test sample with the protein binding profile of a reference sample, whereby the test sample is characterized by the comparison.

In another aspect, the invention provides methods for characterizing a test sample, said methods comprising comparing a protein binding profile of the test sample with a protein binding profile of a reference sample, whereby the test sample is characterized by the comparison; wherein the protein binding profiles are prepared by a method comprising (a) contacting a sample with any of the sets of digital antibodies described herein under conditions that permit binding; (b) optionally removing unbound protein; (c) detecting binding of protein to antibodies, whereby a protein binding profile is generated.

In another aspect, the invention provides methods for characterizing a test sample (such as a test sample suspected of comprising a sample of interest), said methods comprising (a) contacting the test sample with any of the sets of digital antibodies described herein under conditions that permit binding; (b) optionally removing unbound protein;

(c) detecting binding of protein to antibodies, whereby a protein binding profile is generated; and (d) comparing the protein binding profile of the test sample with a library of protein binding profiles generated by any of the methods described herein, whereby the test sample is characterized using the comparison.

In another aspect, the invention provides methods for characterizing a test sample, said methods comprising comparing protein binding profile of the test sample with a library of protein binding profiles, whereby the test sample is characterized by the comparison; wherein the protein binding profiles are prepared by a methods comprising (a) contacting the test sample with any of the sets of digital antibodies described herein under conditions that permit binding; (b) optionally removing unbound protein; (c) detecting binding of protein to antibodies, whereby a protein binding profile is generated; and further wherein the library of protein binding profiles was generated using any of the methods described herein.

In some embodiments, characterizing comprises characterization of a cell, bacteria or virus (including protein or protein fraction derived from cell, bacteria and/or virus) in a sample. In other embodiments, characterizing comprises classification of a cell in a sample, as, e.g., cancerous or precancerous, or a bacteria in a sample (e.g., as pathogenic or non-pathogenic, and/or taxonomic classification). In some embodiments, the type, stage, grade, and/or other relevant diagnostic (and/or prognostic) characteristic of a cancer is determined.

In another aspect, the invention provides methods for determining presence or absence of and/or identifying a sample of interest, said methods comprising (a) contacting a test sample suspected of comprising the sample of interest with any of the sets of digital antibodies described herein under conditions that permit binding; (b) optionally removing unbound protein; (c) detecting binding of protein to antibodies, whereby a protein binding profile is generated; and (d) comparing the protein binding profile of the test sample with the protein binding profile of a reference sample, whereby presence or absence and/or identity of the sample of interest is determined by the comparison.

In another aspect, the invention provides methods for determining presence or absence of and/or identifying a sample of interest, said methods comprising: comparing the protein binding profile of a test sample suspected of comprising the sample of interest with the protein binding profile of a reference sample, whereby presence or absence and/or identity of the sample of interest is determined by the comparison; wherein the protein binding profiles were generated by a method comprising (a) contacting a sample with any of the sets of digital antibodies described herein under conditions that permit binding; (b) optionally removing unbound protein; (c) detecting binding of protein to antibodies, whereby a protein binding profile is generated.

In another aspect, the invention provides methods for detecting presence or absence of and/or identifying a sample of interest, said methods comprising (a) contacting a test sample suspected of comprising the sample of interest with any of the sets of digital antibodies described herein under conditions that permit binding; (b) optionally removing unbound protein; (c) detecting binding of protein to antibodies, whereby a protein binding profile is generated; and (d) comparing the protein binding profile of the test sample with a library of protein binding profiles generated by any of the methods described herein, whereby presence or absence and/or identity of the sample of interest in the test sample is determined by the comparison.

In another aspect, the invention provides methods for detecting presence or absence of and/or identifying a sample of interest, said methods comprising: comparing a protein binding profile of a test sample suspected of comprising the sample of interest with a library of protein binding profiles generated by any of the methods described herein, whereby presence or absence and/or identity of the sample of interest in the test sample is determined by the comparison; wherein the protein binding profile of the test sample is generated by a method comprising: (a) contacting a test sample suspected of comprising the sample of interest with any of the sets of digital antibodies described herein under conditions that permit binding; (b) optionally removing unbound protein; (c) detecting binding of protein to antibodies, whereby a protein binding profile is generated; and the library of protein binding profiles is generated using any of the methods described herein.

In another aspect, the invention provides methods for determining presence or absence of and/or identifying a cell, bacteria, and/or virus in a test sample, said methods comprising (a) contacting the test sample with any of the sets of digital antibodies described herein under conditions that permit binding; (b) optionally removing unbound protein; (c) detecting binding of protein to antibodies, whereby a protein binding profile is generated; and (d) comparing the protein binding profile of the test sample with the protein binding profile of a reference sample, whereby presence or absence and/or identity of the cell, bacteria or virus in the test sample is determined by the comparison.

In another aspect, the invention provides methods for determining presence or absence of and/or identifying a cell, bacteria and/or virus, said methods comprising: comparing the protein binding profile of a test sample suspected of comprising the cell, bacteria and/or virus with the protein binding profile of a reference sample, whereby presence or absence and/or identity of the cell, bacteria or virus is determined by the comparison; wherein the protein binding profiles were generated by a method comprising (a) contacting a sample with any of the sets of digital antibodies described herein under conditions that permit binding; (b) optionally removing unbound protein; (c) detecting binding of protein to antibodies, whereby a protein binding profile is generated.

In another aspect, the invention provides methods for detecting presence or absence of and/or identifying a cell, bacteria and/or virus in a test sample, said methods comprising (a) contacting the test sample with any of the sets of digital antibodies described herein under conditions that permit binding; (b) optionally removing unbound protein; (c) detecting binding of protein to antibodies, whereby a protein binding profile is generated; and (d) comparing the protein binding profile of the test sample with a library of protein binding profiles generated by any of the methods described herein, whereby presence or absence and/or identity of the cell, bacteria or virus in the test sample is determined by the comparison.

In another aspect, the invention provides methods for detecting presence or absence of and/or identifying a cell, bacteria and/or virus, said methods comprising: comparing a protein binding profile of a test sample suspected of comprising the cell, bacteria and/or virus with a library of protein binding profiles generated by any of the methods described herein, whereby presence or absence and/or identity of the cell, bacteria or virus in the test sample is determined by the comparison; wherein the protein binding profile of the test sample is generated by a method comprising: (a) contacting a test sample suspected of comprising the sample of interest with any of the sets of digital antibodies described herein under conditions that permit binding; (b) optionally removing unbound protein; (c) detecting binding of protein to antibodies, whereby a protein binding profile is generated; and the library of protein binding profiles is generated using any of the methods described herein.

In another aspect, the invention provides methods for identifying a test protein, said methods comprising (a) contacting a sample comprising the test protein with any of the sets of digital antibodies described herein; (b) optionally removing unbound protein; (c) detecting presence or absence of binding of protein to antibodies in the set, wherein at least about six digital antibodies bind protein; wherein presence of binding indicates presence of at least about six epitopes in the protein, wherein the identity (i.e., linear amino acid sequence) of the at least about six epitopes is used to identify the protein.

In another aspect, the invention provides methods for identifying a test protein, said methods comprising detecting presence or absence of binding of protein with any of the sets of digital antibodies described herein, wherein at least about six digital antibodies bind protein, wherein presence of binding indicates presence of at least about six epitopes in the protein, wherein the identity (i.e., linear amino acid sequence) of the at least about six epitopes is used to identify the protein; wherein the binding of protein is generated using a method comprising (a) contacting a sample comprising the test protein with any of the sets of digital antibodies described herein; (b) optionally removing unbound protein; (c) detecting presence or absence of binding of protein to antibodies in the set. In some embodiments, the test protein consists of about 500 amino acids in length.

In another aspect, the invention provides methods for identifying a test protein, said methods comprising identifying the test protein based on the identity of at least about six epitopes recognized by at least 6 digital antibodies, wherein the at least about six digital antibodies bind protein, wherein binding of protein to antibodies is detected by a method comprising (a) contacting a sample comprising the test protein with any of the sets of digital antibodies described herein; (b) optionally removing unbound protein; (c) detecting presence or absence of binding of protein to antibodies in the set, wherein at least about six digital antibodies bind protein.

In some embodiments, the binding and epitope identity of about 7, about 8, about 9, about 10, about 11, about 12, about 13, about 14, about 15, about 20, about 25, about 30, or more (such as about 40, 50, 60, or more) digital antibodies is used to identify the test protein. In some embodiments, the methods further comprise the comparison of the epitope identity information (i.e., linear amino acid sequence bound by the antibody) with a database comprising protein sequence information (such as sequences of nucleotides or amino acids). In some embodiment, the sample comprises pure protein. In other embodiments, the sample comprises substantially pure protein.

In another aspect, the invention provides methods for screening, and methods for characterizing, detecting presence or absence of and/or identifying protein complexes, as further described herein.

An antibody can encompass monoclonal antibodies, polyclonal antibodies, antibody fragments (e.g., Fab, Fab', F(ab')$_2$, Fv, Fc, etc.), chimeric antibodies, single chain (ScFv), mutants thereof, fusion proteins comprising an antibody portion, and any other polypeptide that comprises an antigen recognition site of the required specificity. The antibodies may be murine, rat, rabbit, chicken, human, or of any other origin (including humanized antibodies).

As used herein, "sample" encompasses a variety of sample types and/or origins, such as blood and other liquid samples of biological origin, solid tissue samples such as a biopsy specimen or tissue cultures or cells derived therefrom, and the progeny thereof. The term "sample" encompasses a clinical sample, and also includes cells in culture, cell supernatants, cell lysates, serum, plasma, biological fluid, and a pure or enriched bacterial or viral sample derived from any of these, for example, as when a sample is cultured in order to increase, enrich and/or substantially purify a bacterial or viral sample therefrom (or, in some embodiments, to increase amount of a sample comprising bacteria and/or virus). A sample can be from a microorganism, e.g., bacteria, yeasts, viruses, viroids, molds, fungi, plants, animals, including mammals such as humans. A sample may comprise a single cell or more than a single cell. These samples can be prepared by methods known in the art such as lysing, fractionation, purification, including affinity purification, FACS, laser capture microdissection (LCM) or isopycnic centrifugation. In some embodiments, subcellular fractionation methods are used to create enriched cellular or subcellular fractions, such as subcellular organelles including nuclei, mitochondria, golgi apparatus, endoplasmic reticulum, chloroplasts, heavy and light membranes and cytoplasm. In one embodiment, the sample comprises substantially intact protein complexes. In some embodiments, the protein complex is a receptor-associated protein complex or a signal transduction associated protein complex prepared from, e.g., nucleic acid associated receptors (e.g., the estrogen receptor), or membrane associate receptors (e.g., epidermal growth factor receptor, IL-6 receptor, stress/apoptosis pathways, chemokine pathways, MMP transcription pathway,) or cell cycle pathways.

In another aspect, the invention provides a hybridoma producing a digital antibody selected from hybridomas 2.04, 2.03, or 2.11. In some embodiments, the invention provides an digital antibody generated by hybridoma 2.04, 2.03, or 2.11. In other embodiments, the invention provides an antibody comprising a heavy chain variable region and/or a light chain variable regions of a digital antibody produced by hybridoma 2.04, 2.03, or 2.11. In still other embodiments, the invention provides an antibody comprising one or more CDR(s) (such as two, three, four, five and/or all six CDRs) of a digital antibody produced by hybridoma 2.04, 2.05, and/or 2.11.

In another aspect, the invention provides compositions comprising any of the sets of digital antibodies described herein. In some embodiments, the compositions are for use in any of the methods described herein. In one embodiment, the invention provides compositions comprising complexes of protein with any of the sets of digital antibodies described herein. In another embodiment, the invention provides a composition comprising any of the sets of digital antibodies described herein, and a sample. In some embodiments, the antibodies are immobilized (linked and/or attached) to a solid or semi-solid surface, such as an array. In other embodiments, the antibodies are labeled antibodies. In some embodiments, the invention provides a compositions comprising a sets of digital antibodies described herein, a sample, and a set of competitor polypeptides, wherein said competitor polypeptides comprise the cognate amino acid sequence(s) of one of more digital antibodies in the set of digital antibodies. In some embodiments, the competitor polypeptides are labeled.

The invention further provides kits comprising any of the sets of digital antibodies described herein. In some embodiments, the kits further comprise instructions for any of the methods described herein. In some embodiments, the antibodies are immobilized (linked and/or attached) to a solid or semi-solid surface, such as an array. In other embodiments, the antibodies are labeled antibodies. In still other embodiments, the kit comprises any of the libraries of protein binding profiles described herein. In still other embodiments, the kit further comprises a label. In still other embodiments, the kit comprises a set of competitor polypeptides, wherein said competitor polypeptides comprise the cognate amino acid sequence(s) of one of more digital antibodies in the set of digital antibodies. In some embodiments, the competitor polypeptides are labeled competitor polypeptide(s).

DETAILED DESCRIPTION OF THE INVENTION

Figure 1:
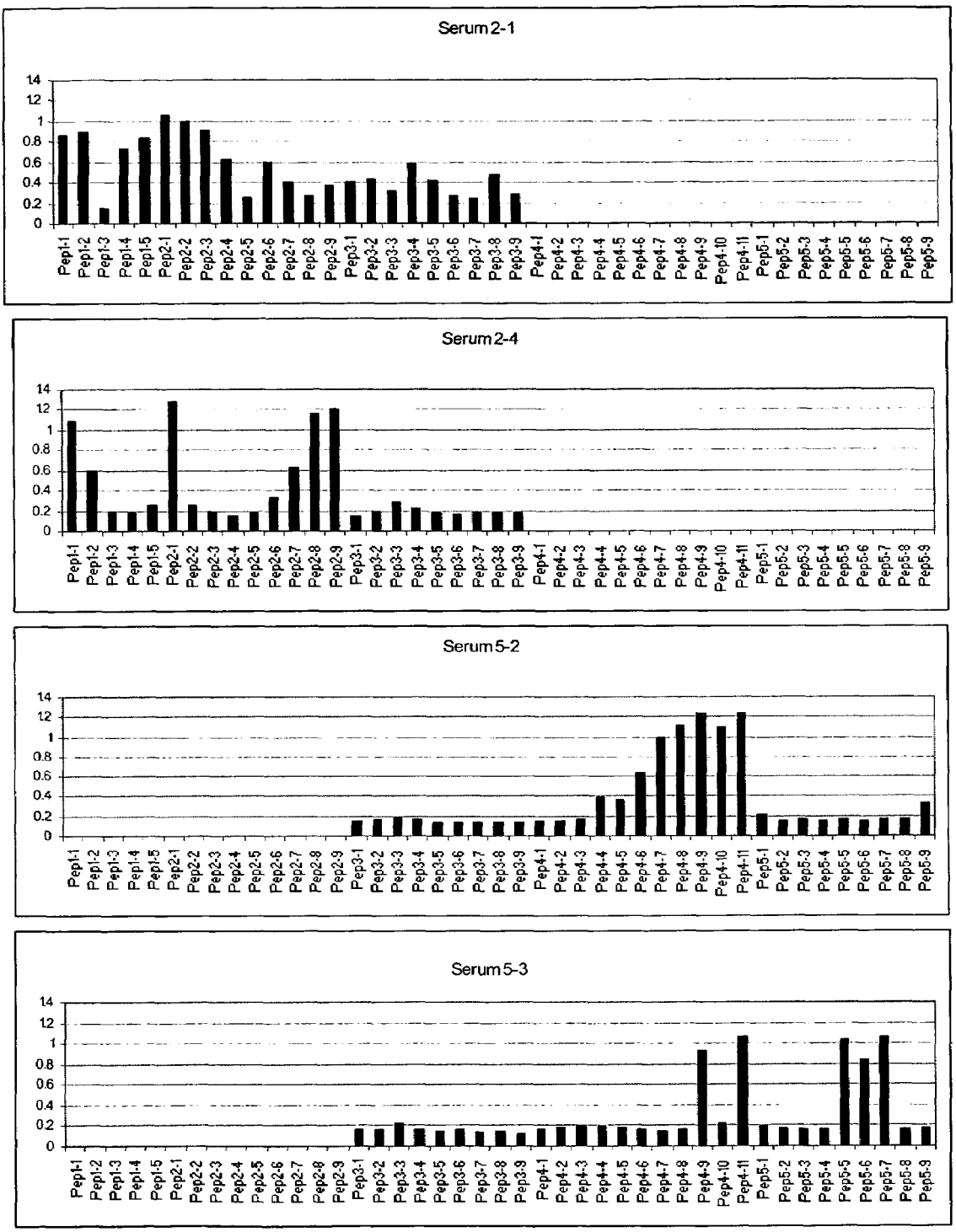
FIG. 1: shows the reaction pattern using mapping polypeptides spanning sequences of immunization polypeptides for group 2 and group 5 mice, respectively.

The present invention stems from the discovery that antibodies that recognize small polypeptide epitopes, often termed "cross-reactive antibodies" in the art, are useful in combination to generate a characteristic pattern of binding between antibodies in a set and protein in a sample, wherein the protein binding pattern, termed a protein binding profile, may be used to characterize, or "fingerprint" the protein sample. The present invention stems from the insight that cross-reactive antibodies (i.e., antibodies that recognize small epitopes, and thus are expected to bind a multiplicity of proteins) may be used in combination to generate a protein binding profile of sufficient specificity such that samples may be characterized, uniquely identified (including identification of one or more components in a sample) and/or distinguished. Thus, specificity of results and information arising from antibody binding is conferred via the binding of sets of digital antibodies to protein in a sample (whereby a specific protein binding profile is generated), rather than by binding of a single antibody that binds but one or a few proteins, as commonly used in the art for specific detection. Generally, a protein binding pattern comprises information regarding presence (or absence) of protein binding and/or intensity (amount) of protein binding between each digital antibody and protein(s) in a sample. The protein binding profile can be used to, e.g., identify the source of the protein sample (e.g., from a pathogen; from a cancer cell), or may be used to identify or detect a previously unknown agent, such as a novel pathogen.

The digital antibodies that recognize small peptide epitopes bind (generally, specifically bind) small linear peptide epitopes consisting of 3 consecutive amino acids, 4 consecutive amino acids, or 5 consecutive amino acids, wherein each antibody in the set binds to a different small linear peptide epitope. Due to the small size of the epitope recognized by a digital antibody (i.e., 3 consecutive amino acids, 4 consecutive amino acids, or 5 consecutive amino acids), a single digital antibody generally binds a plurality of proteins (in some embodiments, a large plurality of proteins) based on the presence of the cognate small epitope within the plurality of bound proteins. Thus, binding of protein to each digital antibody generally reflects binding of a plurality of protein species, each of which possesses one or more copies of the cognate small epitope sequence. Similarly, a single protein may be bound by multiple digital antibodies based on the presence of multiple small epitope sequences within the protein. Generally, the identity of the epitope recognized by a given digital antibody is known, and this information useful, e.g., in methods for identifying proteins as further describe herein.

Accordingly, in one aspect, the invention provides sets of antibodies (termed "digital antibodies") that bind (generally, specifically bind) small linear peptide epitopes consisting of 3 consecutive amino acids, 4 consecutive amino acids, or 5 consecutive amino acids, wherein each antibody in the set binds to a different small linear peptide epitope. It is understood that "different epitopes" encompasses epitopes with overlapping amino acid sequence as well as epitopes with distinct amino acid sequence. In some embodiments, the set comprises at least about 15 digital antibodies, wherein each digital antibody binds a different epitope, and wherein each digital antibody binds an epitope consisting of 3 consecutive amino acids, 4 consecutive amino acids, or 5 consecutive amino acids. In some embodiments, the set comprises at least about any of 20, 30, 40, 50, 60, 70, 80, 90, 100, 110, 125, 150, 175, 200, 300, 400, 500, 600, 700, 800, 900, 1000, or more antibodies. In other embodiments, the set comprises at least about 100 antibodies. In other embodiments, the set comprises at least about 100 digital antibodies that recognize epitopes consisting of 3 consecutive amino acids (also termed a 3mer epitope). In some embodiments, the set comprises at least about 100 digital antibodies that recognize epitopes consisting of 3 consecutive amino acids, and at least about 100 digital antibodies that recognize epitopes consisting of 4 consecutive amino acids (also termed a 4mer epitope). In some embodiments, the set comprises at least about at least about 100 digital antibodies that recognize epitopes consisting of 3 consecutive amino acids, at least about 100 digital antibodies that recognize epitopes consisting of 4 consecutive amino acids, and at least about 100 digital antibodies that recognize epitopes consisting of 5 consecutive amino acids. In another embodiment, the set comprises at least about 1000 digital antibodies that recognize epitopes consisting of 4 consecutive amino acids. Digital antibodies, and methods of making digital antibodies are further described herein.

In another aspect, the invention provides an array comprising any of the digital antibody sets described herein. Methods for generating arrays are well known in the art, and further described herein.

In another aspect, the invention further provides methods using the sets of digital antibodies. As a general overview, the methods involve generating a protein binding profile of a sample using any of the sets of digital antibodies described herein, comprising contacting the sample with a set of digital antibodies, and detection of the antibody-protein complex formed between protein in the sample and antibodies, if any. Detection of the antibody-protein complex provides information relating to amount (intensity) of binding. Detection is performed using methods well known in the art, and further described herein. Thus, the methods for generating a protein binding profile generally comprise (a) contacting a sample with any of the sets of digital antibodies described herein under conditions that permit binding; (b) optionally removing unbound protein (in some embodiments, removing protein that is not specifically bound); and (c) detecting binding of protein to antibodies, whereby a protein binding profile is generated. Generally, binding of a multiplicity of antibodies in a set is detected. In some embodiments, binding of at least about 95%, at least about 90%, at least about 75%, at least about 50%, at least about 30% of antibodies in a set is detected. In some embodiments, binding of each antibody in a set is detected. Detecting may be qualitative and/or qualitative. In some embodiments, the protein binding profile may include (insofar as the small epitope bound by the digital antibody is known) information relating to amino acid content of protein(s) bound by the digital antibod(ies) present in the set of digital antibodies. As further discussed herein, the protein binding profile may be correlated with information relating to the sample, such as source of sample (e.g., of a pathogen such as a bacteria and/or virus, of a cancerous cell or tumor), and may be recorded and stored in a library of protein binding profiles (such as a database).

In some embodiments, the methods of generating a protein binding profile further comprise a step of treating the sample with a protein cleaving agent, whereby polypeptide fragments are generated. The sample can treated with a protein cleaving agent prior to step (a) of contacting the sample with the set of digital antibodies under conditions that permit binding. The protein cleaving agent may be an enzyme (such as chymotrypsin or trypsin) or a chemical agent (such as cyanogen bromide). Protein cleaving agents and methods for treatment with protein cleaving agents are well known in the art and further described herein.

A library of protein binding profiles can be generated by compiling protein binding profiles for two or more different samples, such as samples of pathogenic or non-pathogenic bacteria. The protein binding profiles can be compared with each other, either qualitatively or quantitatively, in order to discern similarities and/or differences in protein binding patterns. The protein binding profiles in the library can also be used in methods involving comparative assessment of the protein binding profiles of sample from different sources (for example, from different tissues or cell types, disease states, or different microorganisms). For example, the libraries of protein binding profiles are useful in methods for characterizing protein samples, methods for diagnosis of bacterial or viral infection, and/or in methods for detection and/or taxonomic classification of a cell, bacteria or infectious agent, as further described herein. For example, a protein binding profile prepared from an unidentified sample may be used to characterize and/or identify the sample by comparison with a library of protein binding profiles (such as a library of known bacterial pathogens).

Thus, in another aspect, the invention provides methods for generating a library of protein binding profiles, comprising the steps of (a) contacting a sample with any of the sets of digital antibodies described herein under conditions that permit binding; (b) optionally removing unbound protein (in some embodiments, removing protein that is not specifically bound); (c) detecting binding of protein to antibodies, whereby a protein binding profile is generated; and (d) repeating steps (a) through (c) with at least two different samples. In some embodiments, the library comprises at least about 5, 10, 15, 20, 25, 30, 35, 40, 45, 50, 75, 100, 150, 200, 300, 400, 500, 600, 700, 800, 900, or more (such as 1000, 2000, 3000, 4000 or more) binding profiles. In another aspect, the invention provides libraries of protein binding profiles, wherein the library is prepared using any of the methods described herein.

In another aspect, the invention provides methods using the protein binding profiles generated according to the methods of the invention (including the libraries of protein binding profiles), including methods involving comparative assessment of the protein binding profiles of sample from different sources (for example, from different tissues or cell types, disease states, or different microorganisms). Thus, the invention provides methods for characterizing a test sample (such as a test sample suspected of comprising a sample of interest); methods for detecting presence or absence and/or identifying a test sample; methods for characterizing a cell, bacteria and/or virus; methods for identifying a test protein; methods for characterizing, detecting presence and/or absence and/or identifying a protein complex; and methods for screening, as further described herein. In some embodiments, the methods involve the comparison of a protein binding profile generated from a test sample with a reference protein binding profile (such as protein binding profile(s) generated from a control sample, or normal values), or library of profiles generated according to any of the methods described herein.

The invention also provides methods for identifying a protein using (a) a protein binding profile generated from a sample comprising the protein; and (b) the amino acid sequences of the epitope recognized by digital antibodies that bind sample protein, whereby binding of a set of digital antibodies (generally, about 6 digital antibodies) provides sufficient information relating to the amino acid content of the protein such that the protein may be identified. By way of example, the simultaneous binding of digital antibodies recognizing the epitopes QAP, TPG, LTG, VSR, and WDQ to a test protein identifies that protein as HCV NS3 protein, for HCV NS3 protein is the only known protein comprising these six 3mer amino acid sequences. Accordingly, in one aspect, the invention provides methods for identifying a test protein, said methods comprising (a) contacting a sample comprising the test protein with any of the sets of digital antibodies described herein; (b) optionally removing unbound protein; (c) detecting presence or absence of binding of protein to antibodies in the set, wherein at least about six digital antibodies bind protein; wherein presence of binding indicates presence of at least about six epitopes in the protein, wherein the identity (i.e., linear amino acid sequence) of the at least about six epitopes is used to identify the protein. In some embodiments, the binding and epitope identity of about 7, about 8, about 9, about 10, about 11, about 12, about 13, about 14, about 15, about 20, about 25, about 30, or more (such as about 40, 50, 60, or more) digital antibodies is used to identify the test protein. In some embodiments, the methods further comprise the comparison of the epitope identity information (i.e., linear amino acid sequence bound by the antibody) with a database comprising protein sequence information (such as sequences of nucleotides or amino acids). In some embodiment, the sample comprises pure protein. In other embodiments, the sample comprises substantially pure protein.

In another aspect, the invention provides methods for screening, and methods for characterizing, detecting presence or absence of and/or identifying protein complexes, as further described herein.

As is evident, one or more steps may be combined and/or performed sequentially (often in any order, as long as the requisite product(s) are able to be formed), and, as is evident, the invention includes various combinations of the steps described herein. It is also evident, and is described herein, that the invention encompasses methods in which the initial, or first, step is any of the steps described herein. Methods of the invention encompass embodiments in which later, "downstream" steps are an initial step.

In another aspect, the invention provides compositions comprising any of the sets of digital antibodies described herein. In some embodiments, the compositions are for use in any of the methods described herein. In one embodiment, the invention provides compositions comprising complexes of protein with any of the sets of digital antibodies described herein. In another embodiment, the invention provides a composition comprising any of the sets of digital antibodies described herein, and a sample. In some embodiments, the antibodies are immobilized (linked and/or attached) to a solid or semi-solid surface, such as an array. In other embodiments, the antibodies are labeled antibodies. In some embodiments, the invention provides a composition comprising a sets of digital antibodies described herein, a sample, and a set of competitor polypeptides, wherein said competitor polypeptides comprise the cognate amino acid sequence(s) of one or more digital antibodies in the set of digital antibodies. In some embodiments, the competitor polypeptides are labeled.

The invention further provides kits comprising any of the sets of digital antibodies described herein. In some embodiments, the kits further comprise instructions for any of the methods described herein. In some embodiments, the antibodies are immobilized (linked and/or attached) to a solid or semi-solid surface, such as an array. In other embodiments, the antibodies are labeled antibodies. In still other embodiments, the kit comprises any of the libraries of protein binding profiles described herein. In still other embodiments, the kit further comprises a label. In still other embodiments, the kit comprises a set of competitor polypeptides, wherein said competitor polypeptides comprise the cognate amino acid sequence(s) of one of more digital antibodies in the set of digital antibodies. In some embodiments, the competitor polypeptides are labeled competitor polypeptide(s).

Methods and conditions for antibody binding and detection of antibody binding are well known in the art and further described herein. In some embodiment, contacting with a set of digital antibodies is sequential (as when one antibody is contacted with the sample, then removed, another antibody is contacted with the sample and removed, and so on). In other embodiments, contacting with a set of digital antibodies is in parallel, for example, as when a group of antibodies are contacted with the sample simultaneously. In some embodiments, several groups of two or more antibodies are serially contacted with the sample, for example, group 1 is contacted and removed, group 2 is contacted and removed, and so on.

An antibody can encompass monoclonal antibodies, polyclonal antibodies, antibody fragments (e.g., Fab, Fab', F(ab')$_2$, Fv, Fc, etc.), chimeric antibodies, single chain (ScFv), mutants thereof, fusion proteins comprising an antibody portion, and any other polypeptide that comprises an antigen recognition site of the required specificity. The antibodies may be murine, rat, rabbit, chicken, human, or of any other origin (including humanized antibodies).

As noted in the definition, and as used herein, "sample" encompasses a variety of protein sample types, including those obtained from an individual (including human and non-human individuals). The sample may also be obtained from food, water, or air. In some embodiments, the sample is a protein sample, such as whole cell protein extract or a subfractionation of the whole cell extract (such as soluble protein, membrane bound protein, periplasmic protein, etc.). In other embodiments, the sample encompasses an intact protein complex, such as a receptor-associated protein complex. In some embodiments, the sample is a pure (or substantially pure) protein, for which identification is desired. Suitable samples for use in the methods of the invention are described further herein. In some embodiments, the sample comprises a protein complex that is isolated and/or substantially purified, e.g., from a cell. In some embodiments, the sample can treated with a protein cleaving agent prior to the step of contacting the sample with the set of digital antibodies under conditions that permit binding. The protein cleaving agent may be an enzyme (such as chymotrypsin or trypsin) or a chemical agent (such as cyanogen bromide). Protein cleaving agents and methods for treatment with protein cleaving agents are well known in the art and further described herein.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; *Oligonucleotide Synthesis* (M. J. Gait, ed., 1984); Methods in Molecular Biology, Humana Press; *Cell Biology: A Laboratory Notebook* (J. E. Cellis, ed., 1998) Academic Press; *Animal Cell Culture* (R. I. Freshney, ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Methods in Enzymology* (Academic Press, Inc.); Handbook of Experimental Immunology (D. M. Weir and C. C. Blackwell, eds.); *Gene Transfer Vectors for Mammalian Cells* (J. M. Miller and M. P. Calos, eds., 1987); *Current Protocols in Molecular Biology* (F. M. Ausubel et al., eds., 1987); *PCR: The Polymerase Chain Reaction* (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: a practical approach* (D. Catty., ed., IRL Press, 1988-1989); *Monoclonal antibodies : a practical approach* (P. Shepherd and C. Dean, eds., Oxford University Press, 2000); *Using antibodies: a laboratory manual* (E. Harlow and D. Lane (Cold Spring Harbor Laboratory Press, 1999); and *The Antibodies* (M. Zanetti and J. D. Capra, eds., Harwood Academic Publishers, 1995).

Definitions

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv), mutants thereof, fusion proteins comprising an antibody portion, and any other modified configuration of the immunoglobulin molecule that comprises an antigen recognition site of the required specificity. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

"Fv" is an antibody fragment that contains a complete antigen-recognition and -binding site. In a two-chain Fv species, this regions consists of a dimer of one heavy and one light chain variable domain in tight, non-covalent association. In a single-chain Fv species, one heavy and one light chain variable domain can be covalently linked by a flexible polypeptide linker such that the light and heavy chains can associate in a dimeric structure analogous to that in a two-chain Fv species. It is in this configuration that the three CDRs of each variable domain interact to define an antigen-binding specificity on the surface of the VH-VL dimer. However, even a single variable domain (or half of a Fv comprising only 3 CDRs specific for an antigen) has the ability to recognize and bind antigen, although generally at a lower affinity than the entire binding site.

A "monoclonal antibody" refers to a homogeneous antibody population wherein the monoclonal antibody is comprised of amino acids (naturally occurring and non-naturally occurring) that are involved in the selective binding of an antigen. A population of monoclonal antibodies (as opposed to polyclonal antibodies) are highly specific, in the sense that they are directed against a single antigenic site. The term "monoclonal antibody" encompasses not only intact monoclonal antibodies and full-length monoclonal antibodies, but also fragments thereof (such as Fab, Fab', F(ab')$_2$, Fv), single chain (ScFv), mutants thereof, fusion proteins comprising an antibody portion, and any other modified configuration of the immunoglobulin molecule that comprises an antigen recognition site of the required specificity and the ability to bind to an antigen (see definition of antibody). It is not intended to be limited as regards to the source of the antibody or the manner in which it is made (e.g., by hybridoma, phage selection, recombinant expression, transgenic animals, etc.).

A "digital antibody" is an antibody that binds (generally specifically binds) a small linear polypeptide epitope consisting of 3 consecutive amino acids, 4 consecutive amino acids, or 5 consecutive amino acids.

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

An epitope that "specifically binds" or "preferentially binds" (used interchangeably herein) to an antibody is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to an epitope is an antibody that binds this epitope with greater affinity, avidity, more readily, and/or with greater duration than it binds to other epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

A "sample" encompasses a variety of sample types, including those obtained from an individual. The definition encompasses blood and other liquid samples of biological origin, solid tissue samples such as a biopsy specimen or tissue cultures or cells derived therefrom, and the progeny thereof. A sample can be from a microorganisms, e.g., bacteria, yeasts, viruses, viroids, molds, fungi, plants, animals, including mammals such as humans, rodents (such as mice and rats), and monkeys (and other primates). A sample may comprise a single cell or more than a single cell. The definition also includes samples that have been manipulated in any way after their procurement, such as by treatment with reagents, solubilization, or enrichment for certain components, such as proteins or polynucleotides. The term "sample" encompasses a clinical sample, and also includes cells in culture, cell supernatants, and cell lysates. Other types of samples are described herein.

"Detect" refers to identifying the presence, absence and/or amount of protein to be detected.

"Absent" or "absence" of binding, and "lack of detection of product" as used herein includes insignificant, or de minimus levels.

An "array" of digital antibodies is an ordered spatial arrangement of one or more antibodies on a physical substrate. Row and column arrangements are preferred due to the relative simplicity in making and assessing such arrangements. The spatial arrangement can, however, be essentially any form selected by the user, and preferably, but need not be, in a pattern.

As used herein, the singular form "a", "an", and "the" includes plural references unless indicated otherwise. For example, "an" antibody includes one or more antibodies and "a protein" means one or more proteins.

Digital Antibody Sets of the Invention

The invention provides sets of digital antibodies, wherein the sets comprise at least about 15 digital antibodies, wherein each digital antibody recognizes a different small linear peptide epitope. As used herein, "digital antibody" is an antibody that binds (generally specifically binds) a small linear peptide epitope consisting of 3 consecutive amino acids, 4 consecutive amino acids or 5 consecutive amino acids. The present invention stems from the insight that antibodies that recognizes small, frequently occurring polypeptide epitopes (often termed "cross-reactive antibodies" in the art) are useful in combination to generate protein binding patterns (such as a pattern of binding to antibodies and/or intensity of binding to antibodies). By virtue of the epitope specificity, digital antibodies generally recognize a multiplicity of proteins that comprise the small epitope to which the antibody binds. Thus, specificity of binding pattern is generated via the binding of sets of digital antibodies to protein in a sample, rather than by binding of a single antibody that binds but one or a few proteins, as commonly used in the art for specific detection. Insofar as the small epitope bound by the antibody is known, binding by a digital antibody provides information relating to amino acid content of protein(s) bound by the digital antibody. Digital antibodies and methods of making digital antibodies are further discussed herein and exemplified in the Examples.

In some embodiments, the set comprises at least about 15 digital antibodies, wherein each digital antibody binds a different epitope, and wherein each digital antibody binds an epitope consisting of 3 consecutive amino acids, or 4 consecutive amino acids. It is understood that "different epitopes" encompasses epitopes that have overlapping amino acid sequences, as well as epitope that have different (non-overlapping) amino acid sequences. In some embodiments, the set comprises at least about 20, 30, 40, 50, 60, 70, 80, 90, 100, 110, 125, 150, 175, 200, 300, 400, 500, 600, 700, 800, 900, 1000, or more antibodies. In other embodiments, the set comprises at least about 100 antibodies. In other embodiments, the set comprises at least about 100 digital antibodies that recognize epitopes consisting of 3 consecutive amino acids (also termed a 3mer epitope). In some embodiments, the set comprises at least about 100 digital antibodies that recognize epitopes consisting of 3 consecutive amino acids, and at least about 100 digital antibodies that recognize epitopes consisting of 4 consecutive amino acids (also termed a 4mer epitope). In some embodiments, the set comprises at least about 100 digital antibodies that recognize epitopes consisting of 3 consecutive amino acids, at least about 100 digital antibodies that recognize epitopes consisting of 4 consecutive amino acids, and at least about 100 digital antibodies that recognize epitopes consisting of 5 consecutive amino acids. In another embodiment, the set comprises at least about 1000 digital antibodies that recognize epitopes consisting of 4 consecutive amino acids. Digital antibodies, and methods of making digital antibodies are further described herein.

An antibody can encompass monoclonal antibodies, polyclonal antibodies, antibody fragments (e.g., Fab, Fab', F(ab')$_2$, Fv, Fc, etc.), chimeric antibodies, single chain (ScFv), mutants thereof, fusion proteins comprising an antibody portion, and any other polypeptide that comprises an antigen recognition site of the required specificity (including antibody mimetics. See, e.g., Xu et al, Chem Biol. 2002 Aug. 9(8):933-42). The antibodies may be murine, rat, rabbit, chicken, human, or any other origin (including humanized antibodies).

As described herein, a digital antibody binds a short, linear peptide epitope of 3, 4, or 5 consecutive (sequential) amino acids. In some embodiments, the digital antibody binds an epitope consisting of 3 sequential amino acids (termed a 3mer), 4 sequential amino acids (termed a 4mer), or 5 sequential amino acids (termed a 5mer). In other embodiments, the digital antibody binds a small discontinuous linear peptide sequence, such as the linear peptide sequence YCxC or YxCC, wherein the "x" represents any of the 20 natural amino acids. Alternatively, "x" may be limited to subset of 2 or more amino acids. It is understood that the amino acid(s) forming the epitope may be linear or branched, and may comprise an amino acid(s) that has been modified naturally or by intervention; for example, disulfide bond formation, glycosylation, lipidation, acetylation, phosphorylation, or any other manipulation or modification, such as conjugation with a labeling component. The amino acid(s) forming the epitope may further encompass, for example, one or more analogs of an amino acid (including, for example, unnatural amino acids, etc.), as well as other modifications known in the art.

Antibodies that bind small linear peptide epitopes have been previously described, as shown in Table 2, below.

In some embodiments, the digital antibody binds its cognate epitope with an affinity of binding reaction of at least about $10^{-7}$ M, at least $10^{-8}$ M, or at least about $10^{-9}$ M, or lower. In some embodiments, a binding interaction will discriminate over adventitious binding interactions in the reaction by at least two-fold, at least five-fold, at least 10- to at least 100-fold or more.

It is understood that other protein binding agents (such as antibodies that are not digital antibodies) may be used, in addition to the digital antibody sets described herein.

It is evident that the number of digital antibodies in the digital antibody set depends on the contemplated uses and applications. Knowledge of the sequence and/or the length of the cognate amino acid epitope recognized by the digital antibody permits an estimate regarding the expected frequency of the epitope(s) recognized by the digital antibodies within the set. As shown in Table 1, there are a total of 8,000 ($20^3$), 160,000 ($20^4$) and 3,200,000 ($20^5$) random combinations for 3mer, 4mer and 5mer linear peptide sequences, respectively. Considering 500 amino acids as an average length of protein, the probability that it is detected by a single anti-3mer antibody is 0.0625, the probability increases to about 1 when 15 anti-3mer antibodies are used, and the probability increases to 6.25 when 100 anti-3mer antibodies are used. Such calculations are routine.

TABLE 1

Distribution properties of short linear amino acid peptides

| | Epitope amino acid length (n) | | | |
|---|---|---|---|---|
| | 2 | 3 | 4 | 5 |
| # of random combinations ($20^n$) | 400 | 8,000 | 160.000 | 3,200,000 |
| Appearance rate in a 500mer protein ($500/20^n$) | 1.25 | 0.0625 | 0.003125 | 0.00015625 |
| Detection rate by 100 anti-nmer antibodies ($100 \times 500/20^n$) | 125 | 6.25 | 0.3125 | 0.015625 |
| Detection rate by 1000 anti-nmer antibodies ($1000 \times 500/20^n$) | 1,250 | 62.5 | 3.125 | 0.15625 |

Thus, it is understood that the number of digital antibodies required in the present invention depends on various factors, including: the use, application, complexity of the sample (in terms of number of expected or estimated or previously determined proteins, including protein variants such as splice variants), average size of the proteins in the sample, frequency that the cognate epitope is present or predicted to be present in a sample; binding affinity and/or specificity of the digital antibody(ies); knowledge of target protein(s); and stability of the digital antibody. Such factors are well known in the art and are further discussed herein.

It is understood that the identity (sequence) of the epitopes to which the digital antibodies bind may be used in combination with any of the methods described herein to, e.g., identify a protein. Generally, at least about 15 to about 18 amino acids of epitope information must be obtained in order to identify a protein. Thus, in some embodiments, at least about 6 anti-3mer digital antibodies, at least about five anti-4mer digital antibodies, or at least about four anti-5mer digital antibodies must bind such that at least about 15-18 amino acids of amino acid epitope information is derived. In some embodiments, at least 6 digital antibodies are used to bind protein of average length of about 500 amino acids.

Digital antibodies may be generated using methods well known in the art.

Antibodies that bind small linear peptide epitopes have been previously described, as shown in Table 2.

TABLE 2

Published short antibody epitope sequence

| Epitope Seq | Source protein | Antibody | Reference |
|---|---|---|---|
| NKS | Opa of N. meningitidis | U623, U506 | Malorny, B., et al. (1998) J Bacteriol 180(5): 1323-30. |
| NRQD | Opa of N. meningitides | O521 | Id. |
| TTFL | Opa of N. meningitides | AB419 | Id. |
| NIP | Opa of N. meningitides | W320/15, W124 | Id. |
| GAT | Opa of N. meningitides | P515 | Id. |
| EQP | MB of U. urealyticum | 3B1.5 | Zheng, X., et al., (1996) Clin Diagn Lab Immunol 3(6): 774-8. |
| WQDE | Porcine ZP3 beta | mAb-30 | Afzalpurkar, A. et al. (1997) Am J Reprod Immunol, 38(1): 26-32. |
| GPGR | Gp120 of HIV-1 | 9x mAbs | Akerblom, L., et al. (1990) Aids 4(10): 953-60. |
| D(A/S)F* | Phosphofructokinase-1 | alpha-F3 | Hollborn, M., et al., (1999) J Mol Recognit, 12(1): 33-7. |
| (D/S)GY(A/G)** | Crotoxin | A-56.36 | Demangel, C., et al., (2000) Eur J Biochem, 267(8): 2345-53 |

*DAF and DSF.
**Refers to DGYA, DGYG, SGYA and SGYG.

In another aspect, and as exemplified in the Examples, digital antibodies (e.g., human, humanized, mouse, chimeric) may be made by using immunogens which express one or more small peptide epitopes, such as a small linear peptide epitope consisting of 3, 4, or 5 amino acids.

Methods for synthesizing polypeptides are well known in the art. In some embodiments, the polypeptide immunogen is synthesized as a multiple antigen polypeptide, or MAP.

The route and schedule of immunization of the host animal are generally in keeping with established and conventional techniques for antibody stimulation and production, as further described herein. General techniques for production of human, mouse, rabbit and chicken antibodies are known in the art and are described herein. Typically, the host animal is inoculated intraperitoneally with an amount of immunogen, including as described herein.

Hybridomas can be prepared from the lymphocytes and immortalized myeloma cells using the general somatic cell hybridization technique of Kohler, B. and Milstein, C. (1975) *Nature* 256:495-497 or as modified by Buck, D. W. et al., (1982) In Vitro, 18:377-381. Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the digital antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce digital antibodies (such as monoclonal antibodies), or a portion thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a human or other species of small epitope receptor, or a fragment of the human or other species of small epitope receptor, or a human or other species of small epitope receptor or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaradehyde, succinic anhydride, SOCl2, or R1N=C=NR, where R and R1 are different alkyl groups can yield a population of antibodies (e.g., monoclonal antibodies).

If desired, the digital antibody (monoclonal or polyclonal) of interest may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity, or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the small epitope and/or greater and/or altered specificity to the small epitope. It will be apparent to one of skill in the art that one or more polynucleotide changes can be made to the digital antibody and still maintain its binding ability to the small epitope.

A number of "humanized" antibody molecules comprising an antigen-binding site derived from a non-human immunoglobulin have been described, including chimeric antibodies having rodent or modified rodent V regions and their associated complementarity determining regions (CDRs) fused to human constant domains. See, for example, Winter et al. *Nature* 349:293-299 (1991), Lobuglio et al. *Proc. Nat. Acad. Sci. USA* 86:4220-4224 (1989), Shaw et al. *J. Immunol.* 138:4534-4538 (1987), and Brown et al. *Cancer Res.* 47:3577-3583 (1987). Other references describe rodent CDRs grafted into a human supporting framework region (FR) prior to fusion with an appropriate human antibody constant domain. See, for example, Riechmann et al. *Nature* 332:323-327 (1988), Verhoeyen et al. *Science* 239:1534-1536 (1988), and Jones et al. *Nature* 321:522-525 (1986). Another reference describes rodent CDRs supported by recombinantly veneered rodent framework regions. See, for example, European Patent Publication No. 519,596. These "humanized" molecules are designed to minimize unwanted immunological response toward rodent anti-human antibody molecules which limits the duration and effectiveness of therapeutic applications of those moieties in human recipients. For example, the antibody constant region can be engineered such that it is immunologically inert (e.g., does not trigger complement lysis). See, e.g. PCT/GB99/01441; UK Patent Application No. 9809951.8. There are four general steps to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; and 6,180,370. Other methods of humanizing antibodies that may also be utilized are disclosed by Daugherty et al., *Nucl. Acids Res.* 19:2471-2476 (1991) and in U.S. Pat. Nos. 6,180,377; 6,054,297; 5,997,867; 5,866,692; 6,210,671; 6,350,861; and PCT Publication No. WO 01/27160.

In yet another alternative, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

In an alternative, antibodies may be made recombinantly and expressed using any method known in the art. In another alternative, antibodies may be made recombinantly by phage display technology. See, for example, U.S. Pat. Nos. 5,565,332; 5,580,717; 5,733,743 and 6,265,150; and Winter et al., *Annu. Rev. Immunol.* 12:433-455 (1994).

Alternatively, the phage display technology (McCafferty et al., *Nature* 348:552-553 (1990)) can be used to produce human antibodies and antibody fragments in vitro, from immunoglobulin variable (V) domain gene repertoires from unimmunized donors. For example, existing antibody phage display libraries may be panned in parallel against a large collection of synthetic polypeptides. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S. and Chiswell, David J., *Current Opinion in Structural Biology* 3, 564-571 (1993). Several sources of V-gene segments can be used for phage display. Clackson et al., *Nature* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Mark et al., *J. Mol. Biol.* 222:581-597 (1991), or Griffith et al., *EMBO J.* 12:725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." Marks, et al., *Bio/Technol.* 10:779-783 (1992)). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., *Nucl. Acids Res.* 21:2265-2266 (1993). Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen-binding site, i.e., the epitope governs (imprints) the choice of partner. When the process is repeated in order to replace the remaining rodent V domain, a human antibody is obtained (see PCT Publication No. WO 93/06213, published Apr. 1, 1993). Unlike traditional humanization of rodent antibodies by CDR grafting, this technique provides completely human antibodies, which have no framework or CDR residues of rodent origin. It is apparent that although the above discussion pertains to humanized antibodies, the general principles discussed are applicable to customizing antibodies for use, for example, in dogs, cats, primates, equines and bovines.

Antibodies may be made recombinantly by first isolating the antibodies made from host animals, obtaining the gene sequence, and using the gene sequence to express the antibody recombinantly in host cells (e.g., CHO cells). Another method that may be employed is to express the antibody sequence in plants (e.g., tobacco), transgenic milk, or in other organisms. Methods for expressing antibodies recombinantly in plants or milk have been disclosed. See, for example, Peeters et al. (2001) *Vaccine* 19:2756; Lonberg, N. and D. Huszar (1995) *Int. Rev. Immunol* 13:65; and Pollock et al. (1999) *J Immunol Methods* 231:147. Methods for making derivatives of antibodies, e.g., humanized, single chain, etc. are known in the art.

Immunoassays and flow cytometry sorting techniques such as fluorescence activated cell sorting (FACS) can also be employed to isolate antibodies that are specific for the desired small epitope.

The antibodies can be bound to many different carriers. Carriers can be active and/or inert. Examples of well-known carriers include polypropylene, polystyrene, polyethylene, dextran, nylon, amylases, glass, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

DNA encoding digital antibodies may be isolated and sequenced, as is known in the art. Generally, the antibody (such as a monoclonal antibody) is readily isolated and sequenced using conventional procedures (e.g., by using oligonucleotide probes that are capable of binding specifically to genes encoding the heavy and light chains of the antibody). The hybridoma cells serve as a preferred source of such cDNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison et al., *Proc. Nat. Acad. Sci.* 81: 6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of a digital antibody (such as a monoclonal antibody) herein.

Digital antibodies may be characterized using methods well-known in the art, some of which are described in the Examples. For example, one method is to identify the epitope to which it binds, including solving the crystal structure of an antibody-antigen complex, competition assays, gene fragment expression assays, and synthetic polypeptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which a digital antibody binds. Epitope mapping is commercially available from various sources, for example, Pepscan Systems (Edelhertweg 15, 8219 PH Lelystad, The Netherlands). Polypeptides of varying lengths (e.g., at least 4-6 amino acids long) can be isolated or synthesized (e.g., recombinantly) and used for binding assays with an anti-digital antibody. In another example, the epitope to which the digital antibody binds can be determined in a systematic screening by using overlapping polypeptides derived from the small epitope extracellular sequence and determining binding by the digital antibody. Certain epitopes can also be identified by using large libraries of random polypeptide sequences displayed on the surface of phage particles (phage libraries), as is well known in the art.

Competition assays can be used to determine whether two antibodies bind the same epitope by recognizing identical or sterically overlapping epitopes. Typically, antigen is immobilized on a multi-well plate and the ability of unlabeled antibodies to block the binding of labeled antibodies is measured. Common labels for such competition assays are radioactive labels or enzyme labels.

The digital antibodies may be linked to an agent (e.g., biotin, oligonucleotide, apatmer), a labeling agent (alternatively termed "label") such as a fluorescent molecule (such as a hapten or fluorescent bead), a solid support (such as a bead or matrix, including a microarray or multiwell plate); or any other agents known in the art. Linking may be covalent or noncovalent. Methods of linking antibodies to such agents are well known in the art. See, e.g. Kennedy et al. (Clin. Chim. Acta 70:1-31 (1976)), and Schurs et al.

(Clin. Chim. Acta 81:1-40 (1977)) (describing coupling techniques, including the glutaraldehyde method, the periodate method, the dimaleimide method, the m-maleimidobenzyl-N-hydroxy-succinimide ester method, all of which methods are incorporated by reference herein). Detection, including suitable labels, is further described herein.

Solid or semi-solid supports suitable for immobilizing, binding and/or linking antibodies (and modifications to render solid supports suitable for immobilizing antibodies) are well known in the art. Examples of a solid support include: a bead (including magnetized beads), microwell plate, a protein microarray (e.g., technology owned by Zyomyx, Inc. See, e.g. U.S. Pat. No. 6,365,418). Thus, for example, CdSe-CdS core-shell nanocrystals enclosed in a silica shell can be easily derivatized for coupling to a biological molecule. Bruchez et al. (1998) Science 281: 2013-2016. Similarly, highly fluorescent quantum dots (zinc sulfide-capped cadmium selenide) have been covalently coupled to biomolecules for use in ultrasensitive biological detection. Warren and Nie (1998) Science 281: 2016-2018. Fluorescently labeled beads are commercially available from Luminex and Quantum Dot. In addition, pads, film, nanowells, or microfluid channels can also serve as a solid support. In some embodiments, the digital antibodies are immobilized, bound or linked on a solid or semi-solid surface such as polyvinylidene difluoride, nitrocellulose, agarose, and/or polyacrylamide gel pads. Glass slides activated with aldehyde, polylysine, or a homofunctional cross-linker can also been used. In some embodiments, the digital antibodies can be arranged in a three-dimensional array, for example in the three dimensional polyacrylamide gel pad microarray described in Mirzabekov et al., Nucleic Acids Res 24(15): 2998-3004 (1996).

Methods Using the Sets of Digital Antibodies

Methods for Generating Protein Binding Profiles

In another aspect, the invention further provides methods using the sets of digital antibodies. The present invention stems from the discovery that antibodies that recognize small polypeptide epitopes, often termed "cross-reactive antibodies" in the art, are useful in combination to generate a characteristic pattern of binding between antibodies in a set and protein in a sample, wherein the protein binding pattern, termed a protein binding profile, may be used to characterize, or "fingerprint" the protein sample. Thus, specificity of results and information arising from antibody binding is conferred via the binding of sets of digital antibodies to protein in a sample (whereby a specific protein binding profile is generated), rather than by binding of a single antibody that binds but one or a few proteins, as commonly used in the art for specific detection.

Figure 2:
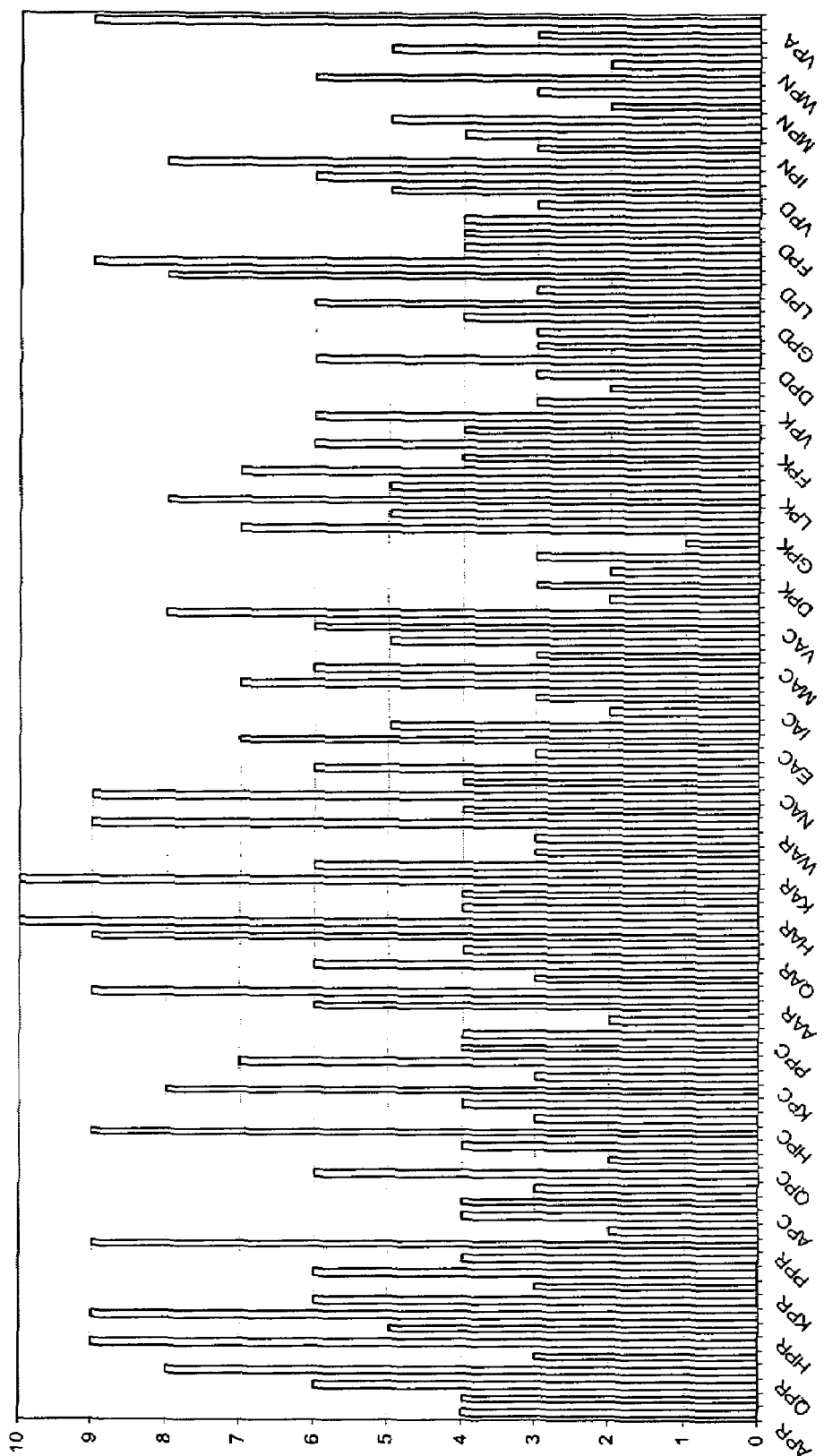
FIG. 2: depicts a computer-simulated protein binding profile prepared using a set of 100 computer-simulated digital antibodies. The X axis corresponds to each of the 100 digital antibodies, and the Y axis represents amount of protein bound. Each bar forming the protein binding profile corresponds to the amount of protein bound by each digital antibody.
Figure 3:
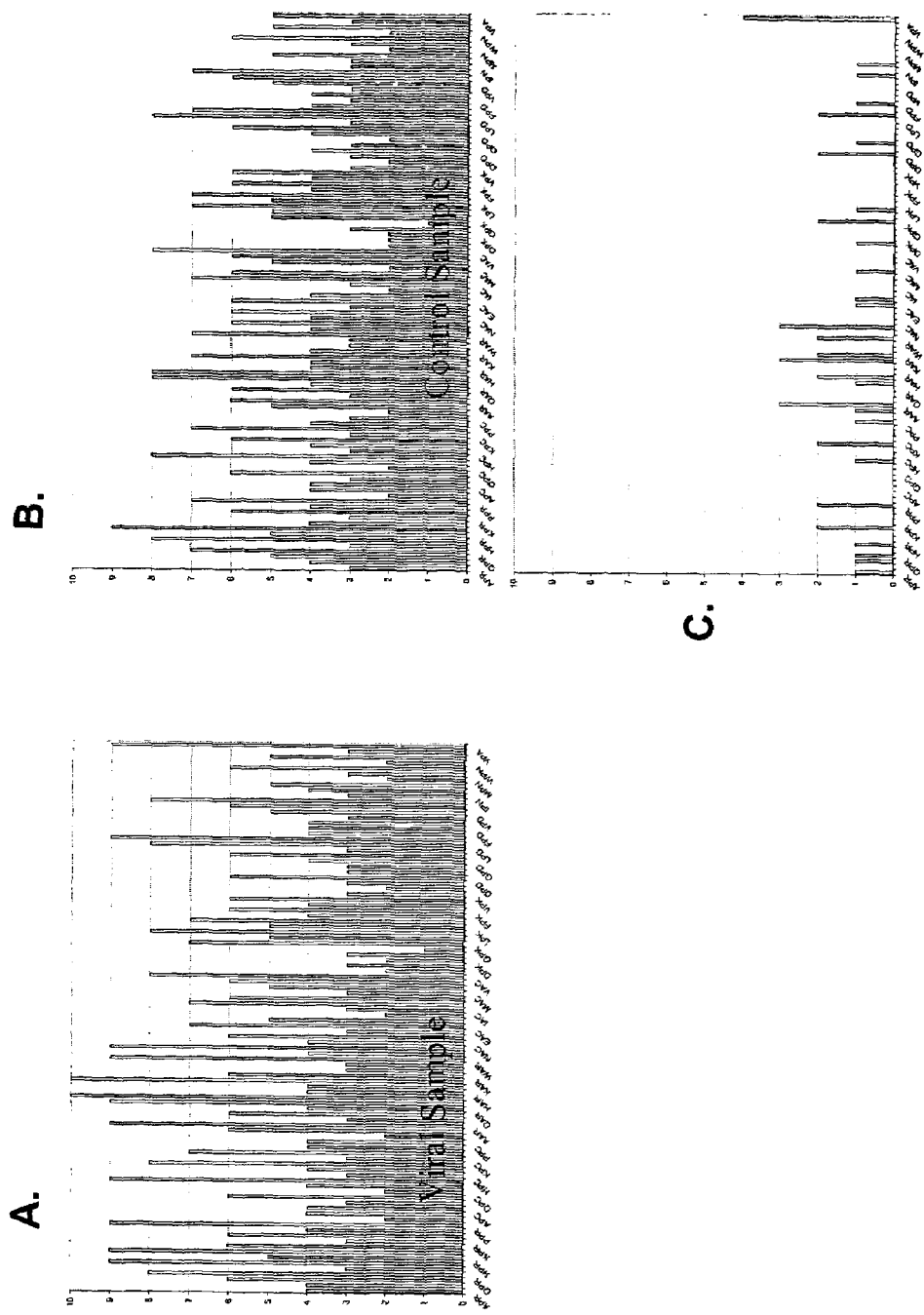
FIG. 3: depicts a computer-simulated protein binding profiles prepared from a simulated sample comprising one or more viral proteins (panel A), and a simulated control sample (panel B), using a computer-simulated set of 100 different digital antibodies. The X axis corresponds to each of the 100 digital antibodies, and the Y axis represents amount of protein bound. Each bar corresponds to the amount of protein bound by each digital antibody. Panel C depicts the protein binding profile following subtraction of the control protein binding profile from the viral sample protein binding profile.

As a general overview, the methods involve generating a protein binding profile of a sample using any of the sets of digital antibodies described herein, comprising (a) contacting the sample with a set of digital antibodies, and (b) detection of the antibody-protein complex formed between protein in the sample and each digital antibody, if any. Detection of the antibody-protein complex may be direct detection, or via indirect detection, such as by using competition assays. Suitable detection methods are well known in the art and described herein. Detection provides information relating to presence or absence of binding, and amount (intensity of binding). Generally, a protein binding pattern comprises information regarding presence (or absence) of protein binding and/or intensity (amount) of protein binding by each digital antibody. FIG. 2 depicts a computer-simulated protein binding profile prepared using a computer-simulated set of 100 different digital antibodies. The X axis corresponds to each of the 100 digital antibodies, and the Y axis represents amount of protein bound. Each bar corresponds to the amount of protein bound by each digital antibody. Additional computer-simulated protein binding profiles are shown in FIG. 3.

Accordingly, in some embodiments, the invention provides methods for generating a protein binding profile of a sample, said methods comprising (a) contacting a sample with any of the sets of digital antibodies described herein under conditions that permit binding; (b) optionally removing unbound protein (in some embodiments, removing protein that is not specifically bound); and (c) detecting binding of protein to antibodies, whereby a protein binding profile is generated. It is understood that a protein binding profile includes information regarding absence of binding between a digital antibody and protein. Detecting may be qualitative and/or qualitative. In some embodiments, protein is labeled, and detection comprises detecting presence, absence and/or amount (intensity) of label on bound protein using methods well known in the art, and described herein. In other embodiments, a competition assay is used, in which labeled peptides (or mixtures of peptides) are used to compete for antibody binding with protein sample. Generally, in embodiments involving use of competitor polypeptides, the methods further comprise contacting the set of digital antibodies with competitor polypeptides (in combination with the sample and/or sequentially with the sample). Detection assay are well known in the art, and further described herein.

Generally, the methods of generating a protein binding profile further comprise a step of treating the sample with a protein cleaving agent, whereby polypeptide fragments are generated. The sample can treated with a protein cleaving agent prior to step (a) of contacting the sample with the set of digital antibodies under conditions that permit binding. The protein cleaving agent may be an enzyme (such as chymotrypsin or trypsin) or a chemical agent (such as cyanogen bromide). Protein cleaving agents and methods for treatment with protein cleaving agents are well known in the art and further described herein.

As further discussed herein, the protein binding profile may be correlated with information relating to the sample, such as source of sample (e.g., of a pathogen such as a bacteria and/or virus). For example, if protein binding patterns have been determined for several members of a family of bacteria, a newly generated pattern can be readily compared to see if it is a member of the family or if it represents a novel member. The protein binding profile may be recorded and stored in a library of protein binding profiles (such as a database), as further discussed herein.

In another aspect, the invention provides a protein binding profile generated using any of the methods described herein.

It is understood that a protein binding profile may be generated without the need to have prior knowledge of the identity of the protein being analyzed, and both known and unknown proteins may be detected. Because information regarding contents of a protein sample is not required, the protein binding profile may be used to identify or detect a previously unknown agent, such as a novel pathogen. For example, a protein binding profile different from that previously seen may indicate a previously unknown agent.

Methods and conditions for antibody binding are well known in the art and further described herein. In some embodiments, contacting with two or more antibodies is sequential (as when one antibody is contacted with the sample, then removed, another antibody is contacted with the sample and removed, and so on). In other embodiments, contacting with a set of digital antibodies is in parallel, for example, as when a group of antibodies are contacted with the sample simultaneously. In some embodiments, several groups of a set of digital antibodies are serially contacted with the sample, for example, group 1 is contacted and removed, group 2 is contacted and removed, and so on.

Methods and conditions for detection of protein-antibody binding are well known in the art. Detection of protein bound to a digital antibody may be qualitative and/or qualitative. Binding of a multiplicity (generally, a large multiplicity) of antibodies in a set is detected. In some embodiments, binding of at least about 95%, at least about 90%, at least about 75%, at least about 50%, or at least about 30% of antibodies in a set are detected. In some embodiments, binding of each antibody in a set is detected. Methods for detection of antibody binding are well known in the art and include, e.g., ELISAs, fluorescent immunoassays, Western and dot blots, immunoprecipitations, competition assays using competitor polypeptides, and focal immunoassays. Alterations in protein binding profile can be determined by running parallel tests on test and control samples and noting any differences in results between the samples. Results of ELISAs, for example, can be directly related to the amount of protein present. In some embodiments, the protein is labeled, and the label is detected. In other embodiments, competitor polypeptides (as further described herein) and labeled, and binding of competitor polypeptides is detected. Suitable labels are well known in the art, and further described herein.

Methods for Generating Libraries of Protein Binding Profiles

A library of protein binding profiles can be generated by compiling protein binding profiles for two or more different samples, such as samples of pathogenic or non-pathogen bacteria. The protein binding profiles can be compared with each other, either qualitatively or quantitatively, in order to discern similarities and/or differences in protein binding patterns. The protein binding profiles in the library can also be used in methods involving comparative assessment of the protein binding profiles of sample from different sources (for example, from different tissues or cell types, disease states, or different microorganisms). For example, the libraries of protein binding profiles are useful in methods for characterizing protein samples, methods for diagnosis of bacterial or viral infection, and/or in methods for detection and/or taxonomic classification of a bacteria or infectious agent, as further described herein. For example, a protein binding profile prepared from an unidentified sample may be used to characterize and/or identify the sample by comparison with a library of protein binding profiles of known bacterial pathogens.

Thus, in another aspect, the invention provides methods for generating a library of protein binding profiles, comprising the steps of (a) contacting a sample with any of the sets of digital antibodies described herein under conditions that permit binding; (b) optionally removing unbound protein (in some embodiments, removing protein that is not specifically bound); (c) detecting binding of protein to antibodies, whereby a protein binding profile is generated; and (d) repeating steps (a) through (c) with at least two different samples. In some embodiments, the library comprises at least about 5, 10, 15, 20, 25, 30, 35, 40, 45, 50, 75, 100, 150, 200, 300, 400, 500, 600, 700, 800, 900, or more (such as 1000, 2000, 3000, 4000 or more) binding profiles. In some embodiments, the methods further comprise step of treating the sample with a protein cleaving agent prior to step (a) of contacting the sample with the set of digital antibodies under conditions that permit binding. In some embodiments, the library further comprises epitope identity information as described herein.

In another aspect, the invention provides libraries of protein binding profiles, wherein the library is prepared using any of the methods described herein.

It is understood that the library of protein binding profiles may comprise binding profiles that were generated at different times, by different individual, and/or at different facilities. In some embodiments, the binding profiles are generated at the same time or different times, and are later grouped together into different libraries. A library of binding profiles can constantly be updated when a new binding profile is generated.

As is well known in the art, a library of binding profiles can be processed using software and stored in a database. The database can be constantly updated as more samples are analyzed and more binding profiles are generated. The binding profiles can be categorized through various methods, such as by the source of the sample, similarity of the binding profiles, etc. For example, the binding profile of bacteria samples may be grouped together based on their phenotypes or genotypes. Additionally, existing taxonomic classifications can be relied on in grouping the binding profiles. In some embodiments, the library comprises protein binding profiles generated from a sample comprising or derived from a prokaryotic cell, such as a bacterium, an eukaryotic cell, such as a cancer or precancerous cell, and/or other microorganisms, such as a virus (including diagnosis of bacterial and/or viral infection).

In another aspect, the invention provides libraries of protein binding profiles generated using any of the methods described herein.

Methods Using the Protein Binding Profiles

In another aspect, the invention provides methods using the protein binding profiles (including libraries of protein binding profiles) generated according to the methods of the invention. Thus, the invention provides methods for characterizing a test sample (such as a test sample suspected of comprising a sample of interest); methods for detecting presence or absence and/or identifying a test sample; methods for characterizing a cell, bacteria and/or virus; methods for identifying a test protein; methods for characterizing, detecting presence and/or absence and/or identifying a protein complex; and methods for screening, as further described herein.

Methods for Identifying a Protein Using Protein Binding Profile and Epitope Amino Acid Sequences The invention also provides methods for identifying a protein using (a) a protein binding profile generated from a sample comprising the protein; and (b) the amino acid sequences of the epitope recognized by digital antibodies that bind sample protein, whereby binding of a set of about 5 or more (such as about 6, about 7, about 8, or more) digital antibodies (generally, providing about 15-18 of amino acid sequence information) provides sufficient information relating to the amino acid content of the protein such that the protein may be identified. By way of example, the simultaneous binding of digital antibodies recognizing the epitopes QAP, TPG, LTG, VSR, and WDQ to a test protein identifies that protein as HCV NS3 protein, for HCV NS3 protein is the only known protein comprising these six 3mer amino acid sequences.

Accordingly, in one aspect, the invention provides methods for identifying a test protein, said methods comprising (a) contacting a sample comprising the test protein with any of the sets of digital antibodies described herein; (b) optionally removing unbound protein; (c) detecting presence or absence of binding of protein to antibodies in the set, wherein at least about five digital antibodies bind protein; wherein presence of binding indicates presence or absence of at least about five epitopes in the protein, wherein the identity (i.e., linear amino acid sequence) (and, in some embodiments, amount) of the at least about five epitopes is used to identify the protein. In some embodiments, the binding and epitope identity (i.e., amino acid sequence of cognate small epitope) of about 6, about 7, about 8, about 9, about 10, about 11, about 12, about 13, about 14, about 15, about 20, about 25, about 30, or more (such as about 40, 50, 60, or more) digital antibodies are used to identify the test protein.

In some embodiments, the methods further comprise the comparison of the epitope identity data with a database comprising protein sequence information (such as sequences of nucleotides or amino acids). The database may consist of nucleotide or amino acid sequences of expressed sequence tags (ESTs). Alternatively, the database may consist of sequences of genes at the nucleotide or amino acid level. The database can include, without limitation, a collection of nucleotide sequences, amino acid sequences, or translations of nucleotide sequences included in the genome of any species. A database of information relating to proteins, e.g., sequences of nucleotides or amino acids, is typically analyzed via a computer program or a search algorithm which is optionally performed by a computer. Information from sequence databases is searched for best matches with data and information obtained from the methods of the present invention (see e.g., Yates (1998) J. Mass Spec. 33: 1-19; Yates et al., U.S. Pat. No. 5,538,897; Yates et al., U.S. Pat. No. 6,017,693). Any appropriate algorithm or computer program useful for searching a database can be used. Search algorithms and databases are constantly updated, and such updated versions will be used in accordance with the present invention. Examples of programs or databases can be found on the World Wide Web (WWW) at http://base-peak.wiley.com/, http://mac-mann6.embl-heidelberg.de/MassSpec/Software.html, http://www.mann.embl-heidelberg.de/Services/PeptideSearch/PeptideSearchIn-tro.html, ftp://ftp.ebi.ac.uk/pub/databases/, and http://donatello.ucsf.ed-u. U.S. Pat. Nos. 5,632,041; 5,964,860; 5,706,498; and 5,701,256 also describe algorithms or methods for sequence comparison. Other examples of databases include the Genpept database, the GenBank database (described in Burks et al. (1990) Methods in Enzymology 183: 3-22, EMBL data library (described in Kahn et al. (1990) Methods in Enzymology 183:23-31, the Protein Sequence Database (described in Barker et al. (1990) Methods in Enzymology 183: 31-49, SWISS-PROT (described in Bairoch et al. (1993) Nucleic Acids Res., 21: 3093-3096, and PIR-International (described in (1993) Protein Seg. Data Anal. 5:67-192). In some embodiments, the present invention also provides methods of determining the identity of a protein wherein a programmable digital computer is used to access a database containing one or more protein sequence databases. In some embodiments, the database further comprises epitope sequence information (i.e., the sequences of cognate small epitopes recognized by a set of digital antibodies). In another aspect, the invention provides a database comprising epitope sequence information, for use in any of the methods for identifying proteins described herein.

The protein sample may comprise pure protein, or, in some embodiments, a substantially pure protein. It is generally understood that the protein sample can be a protein sample prepared from a variety of sources described herein. In some embodiments, a protein binding profile generated from a test sample suspected of comprising a protein of interest (e.g., a bacterial or viral protein) is compared with a protein binding profile generated from a reference sample (i.e., a control sample), and the difference between the profiles is analyzed for epitope binding and epitope identity information as described above, wherein a protein of interest is identified. As an example, FIG. 3 depicts a computer-simulated protein binding profiles prepared from a sample comprising one or more viral proteins (panel A), and a control sample (panel B), using a computer-simulated set of 100 different digital antibodies. The X axis corresponds to each of the 100 digital antibodies, and the Y axis represents amount of protein bound. Each bar corresponds to the amount of protein bound by each digital antibody. Panel C depicts the protein binding profile following subtraction of the control protein binding profile from the viral sample protein binding profile.

Methods Comprising Detection

The invention provides methods for detecting (including diagnosing), determining presence or absence of, and/or identifying a sample of interest, such as a sample comprising or derived from cell, such as a prokaryotic cell (such as a bacterium, such as a pathogenic bacterium); a eukaryotic cell, a mammalian cell (such as a cancerous or precancerous cell), or detecting and/or diagnosing presence or absence of other infection, contamination, disease, and/or abnormality (including detection of type and/or stage of cancer, or identification of a precancerous cell). In some embodiments, the cell is mammalian (such as human),. In other embodiments, the cell is of non-human mammal (such as cow, horse, or dog). In some embodiments, the cell is human, murine, or primate.

Generally, the methods involve generation of the protein binding profile of a test sample suspect of comprising a sample of interest, such as a sample suspected of comprising a cell, bacteria and/or virus, or a sample for which detection of presence or absence of cell (such as a mammalian cell, such as human), bacteria and/or virus is desired. The protein binding profile of the test sample is compared with the protein binding profile of a known cell, bacteria and/or virus and./or compared to a library of binding profiles, e.g., a library of binding profiles of known bacteria and/or viruses. The existence of significant similarity (including a match) between the test binding profile and the control binding profile (in some embodiments, a member(s) of a library of binding profiles) indicates the presence and/or identity of the sample of interest. Absence of a match may indicate the existence of a previously unidentified sample, for example, a previously unidentified pathogenic microbe, and/or absence of a particular bacteria and/or virus in a sample. As used herein, "absence" encompasses de minimum and/or background levels of binding.

Accordingly, in one aspect, the invention provides methods for determining presence or absence of and/or identifying a sample of interest, said methods comprising (a) contacting a test sample suspected of comprising the sample of interest with any of the sets of digital antibodies described herein under conditions that permit binding; (b) optionally removing unbound protein; (c) detecting binding of protein to antibodies, whereby a protein binding profile is generated; and (d) comparing the protein binding profile of the test sample with the protein binding profile of a reference sample, whereby presence or absence and/or identity of the sample of interest is determined by the comparison.

In another aspect, the invention provides methods for detecting presence or absence of and/or identifying a sample of interest, said methods comprising (a) contacting a test sample suspected of comprising the sample of interest with any of the sets of digital antibodies described herein under conditions that permit binding; (b) optionally removing unbound protein; (c) detecting binding of protein to antibodies, whereby a protein binding profile is generated; and (d) comparing the protein binding profile of the test sample with a library of protein binding profiles generated by any of the methods described herein, whereby presence or absence and/or identity of the sample of interest in the test sample is determined by the comparison.

In one aspect, the invention provides methods for determining presence or absence of and/or identifying a cell, bacteria or virus in a test sample, said methods comprising (a) contacting the test sample with any of the sets of digital antibodies described herein under conditions that permit binding; (b) optionally removing unbound protein; (c) detecting binding of protein to antibodies, whereby a protein binding profile is generated; and (d) comparing the protein binding profile of the test sample with the protein binding profile of a reference sample, whereby presence or absence and/or identity of the cell, bacteria or virus in the test sample is determined by the comparison.

In another aspect, the invention provides methods for detecting presence or absence of and/or identifying a cell, bacteria and/or virus in a test sample, said methods comprising (a) contacting the test sample with any of the sets of digital antibodies described herein under conditions that permit binding; (b) optionally removing unbound protein; (c) detecting binding of protein to antibodies, whereby a protein binding profile is generated; and (d) comparing the protein binding profile of the test sample with a library of protein binding profiles generated by any of the methods described herein, whereby presence or absence and/or identity of the cell, bacteria or virus in the test sample is determined by the comparison.

In another aspect, the invention provides methods for identifying a protein, said method comprising comparing a protein binding profile of the test protein with a protein binding profile of a reference protein, wherein the protein binding profile of the reference protein is correlated with the identity of the reference protein; wherein the identity of the test protein is determined by the comparison; and wherein the protein binding profiles have been generated using any of the methods for generating a protein binding profile described herein.

Rapid and accurate microbial identification is critical in diagnosing diseases, predicting on-coming health hazards, monitoring potential contamination in stored foods and grains, regulating bioprocessing operations, and recognizing environmental contamination, including contamination using biowarfare. In some embodiments, the bacteria and/or virus is pathogenic. In other embodiments, the bacteria and/or virus is not pathogenic. In still other embodiments, the bacteria and/or virus is novel, or is a variant of a previously identified bacteria and/or virus.

In some embodiments, the type, subtype, variant, phylum, class, order, family, genus and/or species of a bacteria is identified. As is well known in the art, the study of microbial protein expression may be useful for determining the relationships between members of a genera and evolutionary relationships between members of different genera. In some embodiments, the helpful degree of homology and relationship between species and between members of different genera may be established. For example, the protein binding profiles of different microbe species can be assembled and compared, and the result can be input into a database and used to generate a family relationship dendrograph based on their protein binding profiles. As is apparent, once a family relationship dendrograph is established, a new microbial sample can be classified based its protein binding profile.

In still other embodiments, protein binding profiles of microbial strains may identify strains exhibiting novel phenotypes, such as chemical resistance, altered mode of pathogenity, or varied response to stress, nutrient limitation or genetic manipulation, can be compared via protein binding profile to correlate relative protein abundances associated with these conditions.

In other embodiments, an absence of significant similarity and/or match between binding profile of a test sample, and known protein binding profiles may identify a new strain or a new variant. In still further embodiments, the new strain/variant can be categorized based on the extent of similarity of the binding profile to other binding profiles.

Preparation of samples, and exemplary samples are described herein and well known in the art. It is understood that a sample comprising bacteria and/or virus can be removed from its source (e.g., an individual, food, air, water, and other environmental samples); grown in culture, whereby the bacteria and/or virus is multiplied, enriched and/or purified (in some embodiments, substantially purified) prior to preparation of protein sample. In some embodiments, proteins are prepared from a whole cell extract. In other embodiments, proteins can be pre-fractionated via subcellular location (e.g., membrane and cytoplasmic) or different physical and functional properties. The protein can also be extracted from the supernatant of the culture. In some embodiments, a viral protein sample is prepared from serum and/or plasma and/or any other suitable body fluid.

In some embodiments, the methods of the invention are used to detect, determine presence or absence or and/or identify a cancer cell and/or tissue, including (in some embodiments) detecting (diagnosis of) cancer type, stage, and/or level of differentiation. In some embodiments, precancerous cells are detected.

Thus, in one aspect, the invention provides methods for determining (diagnosing) presence or absence of and/or identifying cancerous cells or tissue (including identifying type of cancer and/or stage of cancer) in a test sample, said methods comprising (a) contacting the test sample with any of the sets of digital antibodies described herein under conditions that permit binding; (b) optionally removing unbound protein; (c) detecting binding of protein to antibodies, whereby a protein binding profile is generated; and (d) comparing the protein binding profile of the test sample with the protein binding profile of a reference sample, whereby presence or absence and/or identity of the cancerous cells or tissue in the test sample is determined by the comparison.

In another aspect, the invention provides methods for detecting presence or absence of and/or identifying cancerous cells or tissue in a test sample, said methods comprising (a) contacting the test sample with any of the sets of digital antibodies described herein under conditions that permit binding; (b) optionally removing unbound protein; (c) detecting binding of protein to antibodies, whereby a protein binding profile is generated; and (d) comparing the protein binding profile of the test sample with a library of protein binding profiles generated by any of the methods described herein, whereby presence or absence and/or identity of the cancerous cells or tissue in the test sample is determined by the comparison.

Methods for Characterizing a Sample

The protein binding profile may be used to characterize a sample, which generally involves comparative assessment of the protein binding profiles of sample from different sources (for example, from different tissues or cell types, disease states, cells subjected to differential treatment, or different microorganisms). In some embodiments, the methods involve the comparison of a protein binding profile generated from a test sample with a reference protein binding profile (such as protein binding profile(s) generated from a control sample, or normal values), or library of profiles generated using any of the methods described herein.

Thus, in one aspect, the invention provides methods for characterizing a test sample (suspected of comprising a sample of interest), said methods comprising (a) contacting the test sample with any of the sets of digital antibodies described herein under conditions that permit binding; (b) optionally removing unbound protein; (c) detecting binding of protein to antibodies, whereby a protein binding profile is generated; and (d) comparing the protein binding profile of the test sample with the protein binding profile of a reference sample, whereby the test sample is characterized by the comparison.

In another aspect, the invention provides methods for characterizing a test sample (such as a test sample suspected of comprising a sample of interest), said methods comprising (a) contacting the test sample with any of the sets of digital antibodies described herein under conditions that permit binding; (b) optionally removing unbound protein; (c) detecting binding of protein to antibodies, whereby a protein binding profile is generated; and (d) comparing the protein binding profile of the test sample with a library of protein binding profiles generated by any of the methods described herein, whereby the test sample is characterized using the comparison. In some embodiments, characterizing comprises classification of the bacteria or virus in a sample (such as classification into a phylum, class, order, family genus, species, and/or any subtype, variant and/or subgroup thereof). In other embodiments, characterizing comprises classification of a cell in a sample, as, e.g., cancerous or precancerous. In some embodiments, the type, stage, grade, and/or other relevant diagnostic characteristic of the cancer is determined.

Methods for Characterizing Protein Binding Complexes and Screening

Specific protein-protein interactions are important to most cellular functions. Frequently, these protein-protein interactions changes in response to extracellular stimulation. Measurement of protein-protein interactions in a cell can help to validate the physiological significance of the interaction, as well as aid in identifying changes that occur in a cell or organism in response to physiological stimuli (including stimuli due to use of a pharmaceutical drug or other chemical). Accordingly, in one aspect, the present invention provides methods for characterizing protein complexes. Generally, the methods for characterizing protein complexes involves methods for generating protein binding profiles of protein complexes. As a general overview, a protein complex (such as a receptor-associated protein complex, or a signal transduction associated protein complex) is prepared using methods known in the art, and the isolated protein complex, either denatured or in its native condition, and a protein binding profile is generated using any of the methods described herein.

Protein binding profiles generated from isolated protein complexes may be used in any of the methods described herein, such as methods for characterizing a sample (in this case, a sample comprising the protein complex), and methods for detecting presence or absence of and/or identifying a sample.

In another aspect, invention provides methods can be used to test chemical composition to determine whether the chemical composition promotes and/or disrupts one or more interactions within a protein complex. It is believed that a chemical composition that promotes and/or disrupts protein-protein interaction within may constitute a useful pharmaceutical Furthermore, future characterization and/or identification of component(s) within the complex that are reduced, increased, absent when normally present, or present when normally absent, may provide information relating to potential drug targets.

It is contemplated that a cell or population of cells may be contacted with a test chemical composition, protein prepared from the cell(s), and protein binding profiles prepared and analyzed using any of the methods described herein. Accordingly, in one aspect, the invention provides method for screening for a chemical composition that alters protein composition of a sample, said method comprising (a) treating a test sample with a chemical composition; (b) contacting the test sample (or protein prepared and/or enriched and/or purified from the test sample) treated with the chemical composition with any of the sets of digital antibodies described herein under conditions that permit binding; (b) optionally removing unbound protein; (c) detecting binding of protein to antibodies, whereby a protein binding profile is generated; and (d) comparing the protein binding profile of the test sample treated with the chemical composition with a protein binding profile of a reference sample not treated with the chemical composition, whereby the chemical composition is characterized by the comparison.

Libraries and other collections of small molecule chemical compositions are well known in the art.

In some embodiments, the screening methods are useful for studying any protein-protein interactions in a variety of contexts, including formation of functional transcription complexes (e.g., estrogen receptor complexes), signal transduction pathways, cytoskeletal organization (e.g., microtubule polymerization), polypeptide hormone receptor-ligand binding, organization of multi-subunit enzyme complexes, and the like, are of particular interest.

In some embodiments, the protein complexes are isolated based on their size or activity, through traditional methods such as column chromatography. In other embodiments when a DNA/RNA-binding protein complex is to be analyzed, the DNA/RNA sequence to which the complex binds to can be used to isolate the protein complex.

In some embodiment, one of the proteins in the complex is known or identified. The known/identified protein can then serve as a bait to isolate its binding partners. Ideally, endogenous proteins can serve as bait if an antibody or other reagents exist that allow specific isolation of the protein with its bound partners, for example, through affinity chromatography or immunoprecipitation. A more generic way is to "tag" the known or identified protein with a sequence readily recognized by an antibody or ligand specific for the tag. Common affinity tags are known in the art, and include Glutathione S-transferase, His6, Calmodulin-binding peptide, haemaglutinin, myc, and FLAG tags.

Compositions

In another aspect, the invention provides compositions comprising any of the sets of digital antibodies described herein. In some embodiments, the compositions are for use in any of the methods described herein (such as a method for generating a protein binding profile). In some embodiments, the compositions are for use in methods for generating protein binding profiles (including methods for generating libraries of protein binding profiles). In other embodiments, the compositions are for use in methods for characterizing a test sample (such as a test sample suspected of comprising a sample of interest); methods for detecting presence or absence and/or identifying a test sample; methods for characterizing a cell, bacteria and/or virus; methods for identifying a test protein; methods for characterizing, detecting presence and/or absence and/or identifying a protein complex; and methods for screening, as further described herein.

In some embodiments, the invention provides compositions comprising complexes of protein with any of the sets of digital antibodies described herein. In some embodiments, the set of digital antibodies is arrayed. In still other embodiments, the antibodies and/or the protein are labeled. In some embodiments, the antibodies are immobilized (linked and/or attached) to a solid or semi-solid surface, such as an array. In other embodiments, the antibodies are labeled antibodies. In other embodiments, the protein is labeled. In still other embodiments, the antibodies and protein are labeled. In some embodiments, the invention provides compositions comprising any of the sets of digital antibodies described herein, a sample, and a set of competitor polypeptides, wherein said competitor polypeptides comprise the cognate amino acid sequence(s) of one of more digital antibodies in the set of digital antibodies. In some embodiments, the competitor polypeptides are labeled.

Kits

The invention also provides kits comprising any of the sets of digital antibodies described herein. Thus, in some embodiments, the invention provides kits comprising at least about 15 digital antibodies, wherein each digital antibody binds a different epitope, and wherein each digital antibody binds an epitope consisting of 3 consecutive amino acids, 4 consecutive amino acids, or 5 consecutive amino acids. In some embodiments, the kit comprises at least about any of 20, 30, 40, 50, 60, 70, 80, 90, 100, 110, 125, 150, 175, 200, 300, 400, 500, 600, 700, 800, 900, 1000, or more antibodies. In other embodiments, the kit comprises at least about 100 antibodies. In other embodiments, the kit comprises at least about 100 digital antibodies that recognize epitopes consisting of 3 consecutive amino acids (also termed a 3mer epitope). In some embodiments, the kit comprises at least about 100 digital antibodies that recognize epitopes consisting of 3 consecutive amino acids, and at least about 100 digital antibodies that recognize epitopes consisting of 4 consecutive amino acids (also termed a 4mer epitope). In some embodiments, the kit comprises at least about at least about 100 digital antibodies that recognize epitopes consisting of 3 consecutive amino acids, at least about 100 digital antibodies that recognize epitopes consisting of 4 consecutive amino acids, and at least about 100 digital antibodies that recognize epitopes consisting of 5 consecutive amino acids. In another embodiment, the kit comprises at least about 1000 digital antibodies that recognize epitopes consisting of 4 consecutive amino acids. The antibodies may be immobilized and/or linked (attached) to a surface, such as an array. In some embodiments, the kit further comprises a label (such as a label for use in labeling protein). In still other embodiments, the antibodies are labeled. In still other embodiments, the kit comprises competitor polypeptide(s). Generally, competitor polypeptide(s) comprise the amino acid sequences of one or more cognate epitopes recognized by a set of digital antibodies. In some embodiments, the competitor polypeptides are labeled. In some embodiments, the competitor polypeptides are MAPs.

In some embodiments, the kits of digital antibodies further comprise instructions for use of the digital antibodies in any of the methods described herein (such as methods of generating a protein binding profile, including methods for generating libraries of protein binding profiles). In some embodiments, the instructions are for methods for characterizing a test sample (such as a test sample suspected of comprising a sample of interest); methods for detecting presence or absence and/or identifying a test sample; methods for characterizing a cell, bacteria and/or virus; methods for identifying a test protein; methods for characterizing, detecting presence and/or absence and/or identifying a protein complex; and methods for screening. In other embodiments, the instructions are for methods for detecting (including diagnosing), determining presence or absence of, and/or identifying a sample of interest, such as a sample comprising or derived from a prokaryotic cell (such as a bacterium, such as a pathogenic bacterium); a eukaryotic cell (such as a cancerous or precancerous cell), or detecting and/or diagnosing presence or absence of other infection, contamination, disease, and/or abnormality (including detection of type and/or stage of cancer, or identification of a precancerous cell). Instructions supplied in the kits of the invention are typically written instructions on a label or package insert (e.g., a paper sheet included in the kit), but machine-readable instructions (e.g., instructions carried on a magnetic or optical storage disk) are also acceptable.

In some embodiments, the kit comprises an array of digital antibodies, said array comprising any of the sets of digital antibodies described herein. In some embodiments, the antibodies are immobilized (linked and/or attached) to a solid or semi-solid surface, such as an array. In other embodiments, the antibodies are labeled antibodies.

In still other embodiments, the kit comprises any of the libraries of protein binding profiles described herein. In some embodiments, the kit comprises a reference protein binding sequence.

In still other embodiments, the kit further comprises a label. In some embodiments, the label is for labeling protein.

In still other embodiments, the kit comprises a set of competitor polypeptides, wherein said competitor polypeptides comprise the cognate amino acid sequence(s) of one of more digital antibodies in the set of digital antibodies. In some embodiments, the competitor polypeptides are labeled competitor polypeptide(s).

The kits of this invention are in suitable packaging. Suitable packaging includes, but is not limited to, vials, bottles, jars, flexible packaging (e.g., sealed Mylar or plastic bags), and the like. Kits may optionally provide additional components such as buffers and interpretive information.

Reaction Mixtures and Components

Sample

As used herein, "sample" encompasses a variety of sample types and/or origins, such as blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as a subgroup of proteins. The term "sample" encompasses a clinical sample, and also includes cells in culture, cell supernatants, cell lysates, serum, plasma, biological fluid, and a pure or enriched bacterial or viral sample derived from any of these, for example, as when a sample is cultured in order to increase, enrich and/or substantially purify a bacterial or viral sample therefrom (or, in some embodiments, to increase amount of a sample comprising bacteria and/or virus). A sample can be from a microorganism, e.g., bacteria, yeasts, viruses, viroids, molds, fungi, plants, animals, including mammals such as humans. A sample may comprise a single cell or more than a single cell.

These samples can be prepared by methods known in the art such as lysing, fractionation, purification, including affinity purification, FACS, laser capture microdissection (LCM) or isopycnic centrifugation. In some embodiments, subcellular fractionation methods are used to create enriched cellular or subcellular fractions, such as subcellular organelles including nuclei, mitochondria, golgi apparatus, endoplasmic reticulum, chloroplasts, heavy and light membranes and cytoplasm.

In one embodiment, the sample comprises substantially intact protein complexes. In some embodiments, the protein complex is a receptor-associated protein complex or a signal transduction associated protein complex prepared from, e.g., nucleic acid associated receptors (e.g., the estrogen receptor), or membrane associate receptors (e.g., epidermal growth factor receptor, IL-6 receptor, stress/apoptosis pathways, chemokine pathways, MMP transcription pathway,) or cell cycle pathways. Methods for preparing such complexes are well known in the art.

In some embodiments, the sample comprises or is derived from (or suspected of comprising) a pathogenic bacteria, such as *Shigella* species, *Salmonella typhi, Salmonella typhimurium, Yersinia enterocolitica, Yersinia pestis, Vibrio cholerae, Campylobacter jejuni, Helicobacter jejuni, Pseudomonas aeruginosa, Haemophilus influenzae*, and *Bordetella pertussis* (whooping cough), *Vibrio cholerae*, and *E. coli*, including Diarrheagenic *E. Coli*, enteroaggregative *E. coli* (EaggEC), enterohaemorrhagic *E. coli* (EHEC), enteroinvasive *E. coli* (EIEC), enteropathogenic *E. coli* (EPEC) and enterotoxigenic *E. coli* (ETEC), Uropathogenic *E. coli* (UPEC), and neonatal meningitis *E. coli* (NMEC). Other pathogenic bacteria include *Bacilus anthracis, Clostridium botulinum, Francisella tularensis, Burkholderia pseudomallei, Coxiella burnetti*, Brucella species, *Burkholderia mallei, Staphylococcus*, drug-resistant *Streptococcus, Rickettsia prowazekii, Shigella* species, *Salmonella, Listeria monocytogenes, Campylobacter jeluni*, and *Yersinia enterocolitica*.

In other embodiments, the sample comprises or is derived from (or is suspected of comprising) a viruses, such as Hepatitis C Virus, Hepatitis B Virus, Human Immunodeficiency Virus, and Cytomegalovirus. Viruses can also be food and waterborne pathogens, such as Caliciviruses and Hepatitis A viruses. Other viruses of interest include, but not limited to, Variola major (smallpox) and other pox viruses, Arenaviruses (including LCM, Junin viruses, Machupo viruses, Guanarito viruses, Lassa Fever viruses), Bunyaviruses (including Hantaviruses, Rift Valley Fever viruses), Flaviruses (including Dengue viruses), Filoviruses (including Ebola viruses and Marburg viruses), Tickborne hemorrhagic fever viruses (including Crimean-Congo Hemorrhagic fever viruses), Tickborne encephalitis viruses, yellow fever viruses, influenza viruses, Rabies virus, West Nile Viruses, La Crosse viruses, California encephalitis viruses, Venezuelan Equine Encephalomyelitis viruses, Eastern Equine Encephalomyelitis viruses, Western Equine Encephalomyelitis viruses, Japanese Encephalitis Viruses, and Kyasanur Forest Viruses.

It is understood that a sample comprising, e.g., bacteria and/or virus can be removed from its source (e.g., an individual, food, air, water, and other environmental samples); grown in culture, whereby the bacteria and/or virus is multiplied, enriched and/or purified (in some embodiments, substantially purified) prior to preparation of protein sample. Similarly, it is understood that a eukaryotic cell, e.g., cancer cell, may be removed from it natural setting, and cultured or propagated in vitro prior to analysis.

In some embodiments, the sample is comprised of (derived from) mammalian cells (in some embodiments, vertebrate cells), such as human, murine, primate, or rodent. In some embodiments, the cell is of a non-human mammal (in some embodiments, of a non-human vertebrate).

In some embodiments, proteins are prepared from a whole cell extract. In other embodiments, proteins can be pre-fractionated via subcellular location (e.g., membrane and cytoplasmic) or different physical and functional properties. The protein can also be extracted from the supernatant of the culture. In some embodiments, a viral protein sample is prepared from serum and/or plasma and/or any other suitable body fluid. In some embodiments, serum suspected of comprising bacteria and/or virus is depleted of the major serum proteins prior to analysis using digital antibodies. Methods for depleting, reducing and/or removing the major serum proteins are well known in the art.

Prior to contacting the sample with a set of digital antibodies, the sample may also be treated with agents capable of denaturing and/or solubilizing proteins, such as detergents (ionic and non-ionic), chaotropes and/or reducing agent. Such agents are known in the art. The sample can also be heated to denature the proteins. Denaturation of the proteins allows the small epitopes on the proteins to be exposed, thus facilitating the binding of the proteins to the digital antibodies.

In other embodiments, the sample is directly applied to the digital antibodies without first being denatured. For example, analyzing the binding profile of a native protein will permit the study of small epitopes on the surface of the protein, thus providing information about the three dimensional structure of the protein.

Contacting the Sample with a Digital Antibody

Methods and conditions for contacting an antibody with a protein in a sample are well known in the art. Antibodies may be contacted with the sample one at a time or in groups of a set of digital antibodies). In some embodiments, contacting is serial (sequential, or iterative), e.g., a single antibody or group of antibodies is contacted with the sample; separated; and a second antibody or group of antibodies is contacted with the sample, and separated, and so on). In other embodiments, contacting is in parallel, e.g., a group of antibodies is contacted with the sample, and separated. It is appreciated that contacting may be both in parallel and serial, as when different groups of antibodies are serially contacted with a sample. Groups of antibodies may be overlapping in composition (e.g., group 1=antibody A, B, C, D; group 2=antibody B, C, D, E, etc.) or different in composition.

In one embodiment, the set of digital antibodies set is contacted with a blocking agent before they are brought to contact with the sample. Blocking agents serve to block non-specific-binding sites, thus increase the detection sensitivity by reducing the background signal.

In some embodiments involving parallel contacting, it is desirable for digital antibodies to be individually separable, for example, by linking the antibody to detectable distinct beads, use of individually separable binding partners, immobilization of antibody in, e.g., different wells of a multiwell plate, use of antibody arrays, and the like. Insofar as the small epitope bound by the antibody is known, binding by a digital antibody provides information relating to amino acid content of protein(s) bound by the digital antibody. In embodiments wherein knowledge of the cognate small epitope is desired, it may be convenient to individually separate the small antibodies (such that the protein bound by each digital antibody is kept separate). However, individual separation or separability is not required in every embodiment. For example, digital antibodies may be combined in small pools of two or more antibodies that possess overlapping antibody composition, such as (1) antibodies ABC; (2) antibodies CDE; (3) antibodies FGH, and (4) antibodies HIJ. Information regarding presence or absence of a particular small epitope may be inferred based on membership in a particular group.

In some embodiments, suitable controls can be included to, e.g., increase the precision of the detection of binding and/or intensity of binding. For example, such a control can include adding a specific antibody to a protein whose level is known to remain constant among the samples. Since the binding intensity of the control protein will be the same, the amount of proteins present can then be normalized.

Solid supports suitable for immobilizing (linking) antibodies (and modifications to render solid supports suitable for immobilizing antibodies) are well known in the art. Examples of a solid support include: a bead (including magnetized beads), microwell plate, and a protein microarray (e.g., technology owned by Zyomyx, Inc. See, e.g. U.S. Pat. No. 6,365,418). Thus, for example, CdSe—CdS core-shell nanocrystals enclosed in a silica shell can be easily derivatized for coupling to a biological molecule. Bruchez et al. (1998) *Science* 281: 2013-2016. Similarly, highly fluorescent quantum dots (zinc sulfide-capped cadmium selenide) have been covalently coupled to biomolecules for use in ultrasensitive biological detection. Warren and Nie (1998) *Science* 281: 2016-2018. Fluorescently labeled beads are commercially available from Luminex and Quantum Dot. Methods for linking antibodies to such agents are well known in the art. See, e.g. Kennedy et al. (Clin. Chim. Acta 70:1-31 (1976)), and Schurs et al. (Clin. Chim. Acta 81:1-40 (1977)) (describing coupling techniques, including the glutaraldehyde method, the periodate method, the dimaleimide method, the m-maleimidobenzyl-N-hydroxy-succinimide ester method, all of which methods are incorporated by reference herein).

Contact with Protease Cleaving Agent

In some embodiments, the methods of the invention further comprise a step of treating the sample with a protein cleaving agent, whereby polypeptide fragments are generated. In embodiments involving a step of separating protein from the antibody-protein complex, the sample can treated with a protein cleaving agent prior to a step of contacting a sample with the digital antibody set.

Protein cleaving reagent treatment generates protein cleavage fragments (such as polypeptides), which can facilitate subsequent mass spectral analysis of the amount of protein and the identity of proteins in a sample(s). In particular, treatment with a protein cleaving reagent treatment can facilitate the analysis of proteins whose molecular masses exceed 25 kDa. Protein cleaving reagent treatment also may facilitate accessibility and/or access of digital antibodies to a cognate epitope. Protein cleaving agents are well known in the art, and are further discussed herein. In some embodiments, one protein cleaving agent is used. In other embodiments, more than one protein cleaving reagent is used. Conditions for treatment with a protein cleaving agent are well known in the art.

The polypeptide cleaving reagent can be a protease. Example of proteases that can be used as polypeptide cleaving reagents, include, but are not limited to: chymotrypsin, trypsin (arg, lys cleavage sequence), thermolysin (phe, leu, iso, val cleavage sequence), V8 protease, Endoproteinase Glu-C, Endoproteinase Asp-N, Endoproteinase Lys-C, Endoproteinase Arg-C, Endoproteinase Arg-N, Factor Xa protease, thrombin, enterokinase, V5 protease, and the tobacco etch virus protease. Proteases useful in the methods of the invention can be genetically engineered and/or chemically modified to prevent autolysis. It is appreciated that an enzymatic protein cleaving regent (such as a protease) can be modified to facilitate removal of the protease from the polypeptide cleavage products following polypeptide cleavage. Such modifications are known in the art and include: (1) bead-bound (e.g., latex, silica or magnetic bead) protease, (2) haptenated protease, (3) affinity depletion of the protease (with, for example, a bead-bound anti-protease, or bead-bound non-cleavable substrate) and/or (4) size exclusion chromatography.

Polypeptide cleaving reagents can also include chemical substances and compounds that cleave polypeptides and peptide bonds such as cyanogen bromide (which cleaves at methionine residues), hydroxylamine (which cleaves between an Asn and a Gly residue), and acid pH (which can cleave an Asp-Pro bond) (see e.g., Ausubel et al., supra). The activity of the polypeptide cleaving reagent can be inhibited by treating with heat, protease inhibitor, metal chelator (e.g., EGTA, EDTA), etc.

In still further embodiments, phosphatases (e.g., an alkaline phosphatase, an acid phosphatase, a protein serine phosphatase, a protein tyrosine phosphatase, and a protein threonine phosphatase, etc.), lipases, and other enzymes can be employed as protein cleaving reagents.

Detection of Protein Binding Pattern and Comparison of Protein Binding Patterns

The proteins in the sample that bind to the set of digital antibodies can be detected using any means known in the art. In some embodiments, the protein is labeled, using any methods known in the art. The term "label" refers to a composition detectable by spectroscopic, photochemical, biochemical, immunochemical, or chemical means. For example, the target protein may be labeled with one or more labeling moieties to allow detection of both protein-antibody complexes and by comparison the lack of such a complex in the comparison sample. The labeling moieties can include compositions that can be detected by photochemical, spectroscopic, biochemical, immunochemical, chemical, optical, electrical, bioelectronic, etc. means. For example, useful protein labels include $^{32}P$, $^{35}S$, fluorescent dyes, electron-dense reagents, enzymes (e.g., as commonly used in an ELISA), biotin, dioxigenin, or haptens and proteins for which antisera or monoclonal antibodies are available. A wide variety of labels and conjugation techniques are known and are reported extensively in both the scientific and patent literature, and are generally applicable to the present invention for the labeling of proteins. Suitable labels include radionucleotides, enzymes, substrates, cofactors, inhibitors, fluorescent moieties, chemiluminescent moieties, magnetic particles, and the like. Labeling agents optionally include e.g., monoclonal antibodies, polyclonal antibodies, proteins, or other polymers such as affinity matrices, carbohydrates or lipids. Detection of labeled proteins may proceed by any of a number of methods, including immunoblotting, tracking of radioactive or bioluminescent markers, or other methods which track a molecule based upon size, charge or affinity. The particular label or detectable moiety used and the particular assay are not critical aspects of the invention. The detectable moiety can be any material having a detectable physical or chemical property. Such detectable labels have been well developed in the field of gels, columns, and solid substrates, and in general, labels useful in such methods can be applied to the present invention. Thus, a label is any composition detectable by spectroscopic, photochemical, biochemical, immunochemical, electrical, optical or chemical means. Useful labels in the present invention include fluorescent dyes (e.g., fluorescein isothiocyanate, Texas red, rhodamine, and the like), radiolabels (e.g., $^3$H, $^{125}$I, $^{35}$S, $^{14}$C, or $^{32}$p), enzymes (e.g., LacZ, CAT, horse radish peroxidase, alkaline phosphatase and others, commonly used as detectable enzymes, either as marker gene products or in an ELISA).

It will be recognized that fluorescent labels are not to be limited to single species organic molecules, but include inorganic molecules, multi-molecular mixtures of organic and/or inorganic molecules, crystals, heteropolymers, and the like. Thus, for example, CdSe-CdS core-shell nanocrystals enclosed in a silica shell can be easily derivatized for coupling to a biological molecule. Bruchez et al. (1998) *Science* 281: 2013-2016. Similarly, highly fluorescent quantum dots (zinc sulfide-capped cadmium selenide) have been covalently coupled to biomolecules for use in ultrasensitive biological detection. Warren and Nie (1998) *Science* 281: 2016-2018.

The label is coupled directly or indirectly to the protein according to methods well known in the art. Methods for attaching and/or linking (either covalently or noncovalently, directly or indirectly, e.g., via a linker) label to protein are well known in the art. As indicated above, a wide variety of labels may be used, with the choice of label depending on the sensitivity required, ease of conjugation of the compound, stability requirements, available instrumentation, and disposal provisions. Non-radioactive labels are often attached by indirect means. In some embodiments, a ligand molecule (e.g., biotin) is covalently bound to a polymer. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with labeled anti-ligands. Alternatively, any haptenic or antigenic compound can be used in combination with an antibody.

Labels can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, fluorescent green protein, and the like. Chemiluminescent compounds include luciferin, and 2,3-dihydrophthalazinediones, e.g., luminol.

In some embodiments, the sample is labeled. In other embodiments, the antibodies are labeled. In still other embodiments, protein and antibodies are labeled. Means of detecting labels are well known to those of skill in the art. Thus, for example, where the label is a radioactive label, means for detection include a scintillation counter, proximity counter (microtiter plates with scintillation fluid built in), or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDS) or photomultipliers and the like. Similarly, enzymatic labels may be detected by providing appropriate substrates for the enzyme and detecting the resulting reaction product. Finally simple colorimetric labels are often detected simply by observing the color associated with the label. Thus, in various dipstick assays, conjugated gold often appears pink, while various conjugated beads appear the color of the bead.

In some embodiments, competition immunoassay is used for detection, as is well known in the art. Specifically, the test sample can be mixed with labeled small-epitope peptides (i.e., polypeptides comprising one or more cognate small epitopes recognized by one or more members of the set of digital antibodies being used in the assay) and brought into contact with the digital antibodies. The binding signal can then be detected. The signal can further be amplified to increase the sensitivity prior to the detection. Labels that are useful for the present method are known in the art, and include chemiluminescent molecules, magnetic labels, biotin, etc. In embodiments involving use of competitor polypeptides, the methods for generating protein binding profiles (and methods using protein binding profiles) generally further comprise contacting the set of digital antibodies with competitor polypeptides (in combination with the sample and/or sequentially with the sample).

In one embodiment, multiple-epitope inhibitors (such as MAPs) are used in a competition immunoassay. "Multi-epitope inhibitors" used herein refer to synthetic peptides or peptides generated by protein digestion, which contain multiple digital antibody epitopes. These multiple-epitope inhibitors therefore will compete with the protein sample for binding to the digital antibodies. The use of multiple-epitope inhibitor reduces the number of peptides needed for the competition immunoassay.

In another embodiments, digital antibodies are coated or linked to a solid surface, protein (including protein fragments from sample) are labeled, e.g. with biotin before contacting with antibodies, protein is contacted with antibodies, unbound protein is removed, and then streptavidin conjugated enzymes, fluorescent dyes and/or nanocrystals are used to detect protein bound to digital antibodies.

Figure 4:
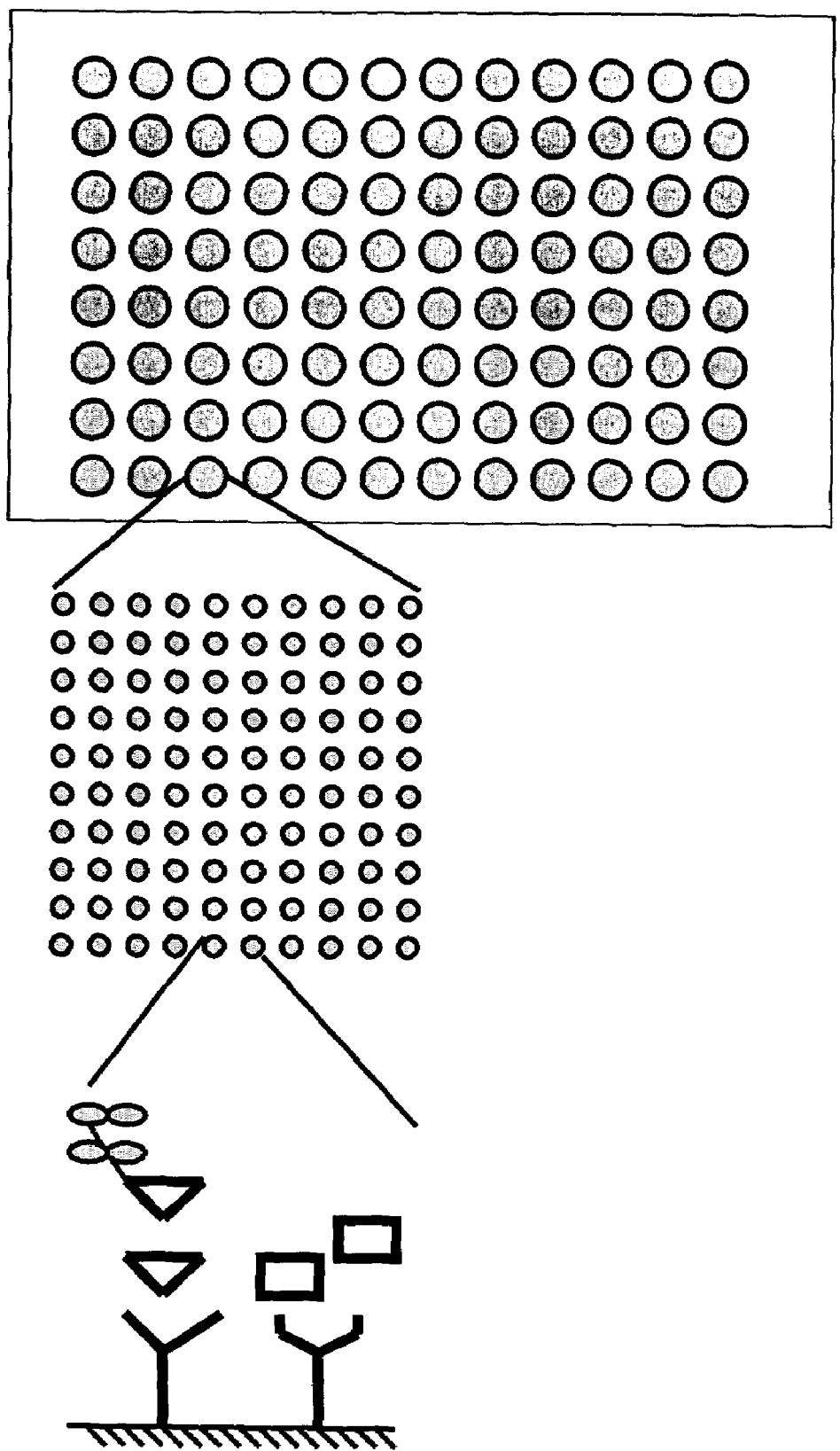
FIG. 4: shows one illustrative embodiment of a digital antibody microarray of the invention. A standard 96-well microtiter plate format will be used in order to fit available automatic high-throughput systems. One hundred to two hundred digital antibodies are coated in each single well in duplicate, forming an array of antibodies within each microwell. Fluorescein or enzyme-labeled single or multiple-epitope inhibitor polypeptides are mixed with trypsin-digested protein sample, and then incubated with the antibodies in a competitive antibody-antigen interaction manner. Signals can be viewed under a fluorescent reader immediately or further amplified by adding enzyme-conjugated anti-fluorescein antibody to increase sensitivity.

In another embodiment, a competition assay is conducted, e.g., by coating or linking digital antibodies to a solid surface, and protein (such as protein fragments) from sample and one or more labeled synthetic peptides are added together or sequentially to the digital antibodies. Each synthetic peptide comprises binding epitopes of two or more digital antibodies used, and the mixture of the synthetic peptides comprises the epitopes of all of the digital antibodies used (in some embodiments, essentially all of the digital antibodies used). The synthetic peptide mixture thus competes for binding with protein (such as protein fragments) in a sample that contains binding epitopes of the digital antibodies in the array. Synthetic peptides (also termed competition peptides) can be labeled using nanocrystals, enzymes and/or fluorescent dye. In some embodiments, the label can be biotin or avidin or streptavidin, and then signal is amplified using avidin, streptavidin or biotin conjugated enzyme, fluorescent dye or nanocrystal will be used to demonstrate the result of the competitive binding. FIG. 4 depicts an illustrative embodiments of a digital antibody array and described a detection embodiments using competition polypeptides.

Data generated by detection of protein binding can be analyzed using any suitable means (e.g., visually, by computer, etc.). In one embodiment, data is analyzed with the use of a programmable digital computer. The data analysis can include the steps of determining the intensity of the signal. The intensity can be normalized, whereby the intensity is calibrated relative to some reference value. For example, a reference can be background noise of the binding. Alternatively, a reference can be the protein binding intensity of a control antibody.

In some embodiments, the intensity of binding of each digital antibody to protein in the sample can be digitized to generate a number. The term "digitized" as used herein, refers to the process of converting the binding signals into digital data. The number representing the intensity of binding of each digital antibody can then be stated in sequence to generate a multi-digit number which represents the binding of the digital antibodies to that sample. In another embodiment, the binding profile is represented by graphical representations similar to a bar graph. In this embodiment, each slot or position of the bar graph represents a specific digital antibody, and the height or width of the "bar" represents the presence and/or absence and/or degree, or intensity, of binding. The generation of these numbers or graphical representations permits the ready storage of information about large set of samples. Moreover, a comparison of two numbers or graphical representations provides information on the degree to which the two samples of interest differ.

The comparison of protein binding profiles can be performed by any convenient means. For example, visual comparisons of patterns can be performed to determine patterns associated with different types of toxicities. More conveniently, the correlation can be done by computer, using one of the database programs discussed in the previous section. Preferably, the correlation is performed by a computer using a neural network program, since neural network programs are specifically designed for pattern recognition. The comparison of protein binding profiles can be done by a number of means known in the art. Usually, the graphs resulting from the calculations can be stored, for example, in file folders or the like, and examined visually to discern common patterns of expression compared to the control, as well as differences. Conveniently, however, the data can be stored on and compared by a computer.

Standard database programs, such as Enterprise Data Management (Sybase, Inc., Emeryville, Calif.) or Oracle8 or 9 (Oracle Corp., Redwood Shores, Calif.) can be used to store and compare information. Alternatively, the data can be recorded, or analyzed, or both, in specifically designed programs available, for example, from Partek Inc. (St. Charles, Mo.).

Additionally, companies selling integrated analytical systems, such as mass spectrometers, provide with the machines integrated software for recording results. Such companies include Finnigan Corp. (San Jose, Calif.), Perkin-Elmer Corp. (Norwalk Conn.), Ciphergen Biosystems, Inc. (Palo Alto Calif.), and Hewlett Packard Corp. (Palo Alto, Calif.).

In a preferred embodiment, the data can be recorded and analyzed by neural network technology. Neural networks are complex non-linear modeling equations which are specifically designed for pattern recognition in data sets. One such program is the NeuroShell Classifier™ classification algorithm from Ward Systems Group, Inc. (Frederick, Md.). Other neural network programs are available from, e.g., Partek, Inc., BioComp Systems, Inc. (Redmond Wash.) and Z Solutions, LLC (Atlanta, Ga.).

The following Examples are provided to illustrate, but not limit, the invention.

EXAMPLES

Example 1

Preparation and Characterization of Digital Antibodies

Five immunization peptides in the format of Multiple Antigenic Peptides (MAPs) were designed as shown in Table 4. These sequences in combination were also used to evaluate cross-reactivity of the induced antibodies, by virtue of the inclusion in different MAPs of the same sequence in differing locations. Each of the immunization peptides were used to immunize 4 Balb/C mice using standard methods.

TABLE 4

Design of immunization peptides

| Peptide | Group | Sequence | SEQ ID NO |
|---------|-------|----------|-----------|
| MAP1 | 1 | Acetylation-HSLFH PEDTGQV KKTTNV-MAP | |
| MAP2 | 2 | Acetylation- PEDTGQV KKTTNVHSLFH-MAP | |
| MAP3 | 3 | Acetylation-LTPKKTTNVLTVP TNIPG MAP | |
| MAP4 | 4 | Acetylation-LTPKK LTQENQNRGTH IYNQ-MAP | |
| MAP5 | 5 | Acetylation-TTYN TNIPG LTQENQNRGTH-MAP | |

Notes to Table 4:

Peptide MAP1: HSLFHPEDTGQV: From PSA, amino acids #79-89. KKTTNV: From Meningococcal Opa protein, containing KTT, a published 3mer antibody epitope (Malorny, Morelli et al. 1998).

Peptide MAP2: Alternate sequences of MAP1.

Peptide MAP3: LTPKK: Motif 1 of PSA (Nagasaki, Watanabe et al. 1999). KKTTNVLTVPTNIPG: From Meningococcal Opa protein, containing two published 3mer antibody epitopes: KTT and NIP and one 4mer epitope: TNIP (Morelli et al. (1997) Mol Microbiol 25(6): 1047-64.

Peptide MAP4: LTPKK: From PSA, the same as in peptide MAP3. LTQENQNRGTH: An immunogenic sequence of alpha-1-ACT selected by DNAStar computer program. IYNQ: From Meningococcal Opa protein, containing a 2mer epitope IY and four amino acids of a 5mer epitope, TIYNQ and of a 7mer epitope TPTIYNQ (Marelli et al, id.).

Peptide MAP5 TIYNTNIPG: From Meningococcal Opa protein (Marelli et al, id.). LTQENQNRGTH: The same as in peptide MAP4.

Two sets of screening peptides were designed: (1) 5 C-terminally biotinylated with the same sequences as the immunization peptides (shown in Table 5); and (2) 43 10mer biotinylated peptides with sequences panning all five immunization peptides (shown in Table 6).

TABLE 5

Biotinylated screening peptides (approximately 90% purity)

| Peptide | Mers | Sequence |
|---|---|---|
| Pep1-0 | 18 | Acetylation-HSLFHPEDTGQVKKTTNV-Biotin |
| Pep2-0 | 18 | Acetylation-PEDTGQVKKTTNVHSLFH-Biotin |
| Pep3-0 | 18 | Acetylation-LTPKKTTNVLTVPTNIPG-Biotin |
| Pep4-0 | 20 | Acetylation-LTPKKLTQENQNRGTHIYNQ-Biotin |
| Pep5-0 | 20 | Acetylation-TIYNTNIPGLTQENQNRGTH-Biotin |

TABLE 6

Forty three 10mer biotinylated mapping peptides (approximately 70% purity)

| Serial number | Peptide name | Sequence | Position in immunization peptides |
|---|---|---|---|
| 1 | Pep1-1 | Acetylated-HSLFHPEDTG-Biotin | MAP1 1-10 |
| 2 | Pep1-2 | Acetylated-SLFHPEDTGQ-Biotin | MAP1 2-11 |
| 3 | Pep1-3 | Acetylated-LFHPEDTGQV-Biotin | MAP1 3-12 |
| 4 | Pep1-4 | Acetylated-FHPEDTGQVK-Biotin | MAP1 4-13 |
| 5 | Pep1-5 | Acetylated-HPEDTGQVKK-Biotin | MAP1 5-14 |
| 6 | Pep2-1 | Acetylated-PEDTGQVKKT-Biotin | MAP1 6-15, MAP2 1-10 |
| 7 | Pep2-2 | Acetylated-EDTGQVKKTT-Biotin | MAP1 7-16, MAP2 2-11 |
| 8 | Pep2-3 | Acetylated-DTGQVKKTTN-Biotin | MAP1 8-17, MAP2 3-12 |
| 9 | Pep2-4 | Acetylated-TGQVKKTTNV-Biotin | MAP1 9-18, MAP2 4-13 |
| 10 | Pep2-5 | Acetylated-GQVKKTTNVH-Biotin | MAP2 5-14 |
| 11 | Pep2-6 | Acetylated-QVKKTTNVHS-Biotin | MAP2 6-15 |
| 12 | Pep2-7 | Acetylated-VKKTTNVHSL-Biotin | MAP2 7-16 |
| 13 | Pep2-8 | Acetylated-KKTTNVHSLF-Biotin | MAP2 8-17 |
| 14 | Pep2-9 | Acetylated-KTTNVHSLFH-Biotin | MAP2 9-18 |
| 15 | Pep3-1 | Acetylated-LTPKKTTNVL-Biotin | MAP3 1-10 |
| 16 | Pep3-2 | Acetylated-TPKKTTNVLT-Biotin | MAP3 2-11 |
| 17 | Pep3-3 | Acetylated-PKKTTNVLTV-Biotin | MAP3 3-12 |
| 18 | Pep3-4 | Acetylated-KKTTNVLTVP-Biotin | MAP3 4-13 |
| 19 | Pep3-5 | Acetylated-KTTNVLTVPT-Biotin | MAP3 5-14 |
| 20 | Pep3-6 | Acetylated-TTNVLTVPTN-Biotin | MAP3 6-15 |
| 21 | Pep3-7 | Acetylated-TNVLTVPTNI-Biotin | MAP3 7-16 |

TABLE 6-continued

Forty three 10mer biotinylated mapping peptides (approximately 70% purity)

| Serial number | Peptide name | Sequence | Position in immunization peptides |
|---|---|---|---|
| 22 | Pep3-8 | Acetylated-NVLTVPTNIP-Biotin | MAP3 8-17 |
| 23 | Pep3-9 | Acetylated-VLTVPTNIPG-Biotin | MAP3 9-18 |
| 24 | Pep4-1 | Acetylated-LTPKKLTQEN-Biotin | MAP4 1-10 |
| 25 | Pep4-2 | Acetylated-TPKKLTQENQ-Biotin | MAP4 2-11 |
| 26 | Pep4-3 | Acetylated-PKKLTQENQN-Biotin | MAP4 3-12 |
| 27 | Pep4-4 | Acetylated-KKLTQENQNR-Biotin | MAP4 4-13 |
| 28 | Pep4-5 | Acetylated-KLTQENQNRG-Biotin | MAP4 5-14 |
| 29 | Pep4-6 | Acetylated-LTQENQNRGT-Biotin | MAP4 6-15, MAP5 10-19 |
| 30 | Pep4-7 | Acetylated-TQENQNRGTH-Biotin | MAP4 7-16, MAP5 11-20 |
| 31 | Pep4-8 | Acetylated-QENQNRGTHI-Biotin | MAP4 8-17 |
| 32 | Pep4-9 | Acetylated-ENQNRGTHIY-Biotin | MNP4 9-18 |
| 33 | Pep4-10 | Acetylated-QENQNRGTHI-Biotin | MAP4 10-19 |
| 34 | Pep4-11 | Acetylated-ENQNRGTHIY-Biotin | MAP4 11-20 |
| 35 | Pep5-1 | Acetylated-TIYNTNIPGL-Biotin | MAP5 1-10 |
| 36 | Pep5-2 | Acetylated-IYNTNIPGLT-Biotin | MAP5 2-11 |
| 37 | Pep5-3 | Acetylated-YNTNIPGLTQ-Biotin | MAP5 3-12 |
| 38 | Pep5-4 | Acetylated-NTNIPGLTQE-Biotin | MAP5 4-13 |
| 39 | Pep5-5 | Acetylated-TNIPGLTQEN-Biotin | MAP5 5-14 |
| 40 | Pep5-6 | Acetylated-NIPGLTQENQ-Biotin | MAP5 6-15 |
| 41 | Pep5-7 | Acetylated-IPGLTQENQN-Biotin | MAP5 7-16 |
| 42 | Pep5-8 | Acetylated-PGLTQENQNR-Biotin | MAP5 8-17 |
| 43 | Pep5-9 | Acetylated-GLTQENQNRG-Biotin | MAP5 9-18 |

After a standard period of immunization, immune sera were collected from each mouse using standard methods, and tested using ELISA as follows: ELISA plates (Coming 3369 or similar) were coated with 100 μl/well or 50 μl/well of streptavidin (Sigma Catalog No. S4762 or similar, 5 μg/ml in 50 mM carbonate buffer, pH 9.6). Plates were incubated at 4° C. overnight or at room temperature for 2 hours. Following incubation, plates were washed 3 times with PBS±0.05% Tween-20 (PBST buffer). Following washing, plates were blocked with 250 μl/well of PBST, and incubate at room temperature for 1 hour, or at 4° C. overnight. PBST was removed, and 100 μl/well or 50 μl/well of 5 μg/ml of a test biotinylated peptide selected from Table 5 (diluted in PBS) was added. Plates were incubated for about 30 to 60 min at room temperature. Following incubation, plates were washed 3 times with PBST. Then, 100 μl or 50 μl/well of test serum (i.e., from test bleeds) was added, and incubated for one hour at room temperature, or overnight at 4° C. To titer immunoreactivity, the serum was generally diluted prior to testing to 1:500, 1:2000, 1:8000, or 1:32000. Following incubation, plates were washed 3 times with PBST. To detect antibody binding, a 1:10,000 dilution of goat anti-mouse IgG (and IgM)-HRP conjugate (Jackson Immuno order No. 115-036-071, or similar) was added to each well. Plates were incubated at room temperature for another hour, then washed 5 times with PBST. HRP substrate (Sigma Fast OPD, catalog No. P-9187) was added and incubated in the dark at room temperature for 30-60 minutes. Plates were read at OD450 with a 96-well colorometric detector if HRP reaction was not stopped. Alternatively, HRP reaction was stopped with 1.25M sulfuric acid, and plates were read at OD492.

12 test bleeds from Groups 1, 2, and 3 mice were tested. No immune response was observed from mice in groups 1 and 3, and these mice were not studied further. All 4 mice in group 2 showed strong immune response to screening peptide Pep2-0 (>1:32,000). In addition, immune sera from two of the four mice in group 2 (mice #2-1 and #2-4) showed cross-reactivity with screening peptides designed for groups 1 and 3 due to the sequence homology between MAP2 and MAP1/MAP3. These results were consistent with mice #2-1 and #2-4 expressing antibodies that recognize distinct and concise epitopes present within more than one screening antigen used in the ELISA assays. A test of the #2-1 and #2-4 sera versus 23 10mer biotinylated peptides that span sequences of all three immunization peptides for group 1, 2 and 3 mice also demonstrated a broad cross-reactivity.

Eight test bleeds from groups 4-5 were tested by ELISA. Group 4 mice demonstrated a modest response to their relevant screening peptide, Pep4-0, while exhibiting strong cross-reactivity with Pep3-0, the screening peptide designed for group 3. Group 4 mice did not show substantial cross-reactivity to Pep5-0 even though there is significant sequence identity between Pep4-0 and Pep5-0. In contrast, 3 of 4 mice in group 5 (mice 5-2, 5-3, 5-4) exhibited robust immunoreactivity to both their screening peptide, Pep5-0, and to the related screening peptide, Pep4-0. The sera from the responsive mice in group 5 did not demonstrate substantial cross-reactivity to the Pep3-0, even though there is a 5 amino acid block of sequence identity. A test of the #5-2 and 5-3 sera versus 23 10mer biotinylated peptides that span sequences of all three immunization peptides for group 4 and 5 mice demonstrated two broad but distinctive reaction patterns with the mapping peptides spanning sequences of immunization peptides for groups 4 and 5 mice.

Group 2 mice #1 and #4, and Group 5 mice #2 and #3 showed the best immune responses, as summarized in Table 7 and FIG. 2. These mice were selected for hybridoma fusions.

TABLE 7

Immunoreactivity and cross-reactivity of selected mice in Groups 2 and 5 to screening peptides 1–5.

| Mouse | Peptide 1 | Peptide 2 | Peptide 3 | Peptide 4 | Peptide 5 |
|---|---|---|---|---|---|
| 2-1 | 0.726 | 0.850 | 0.323 | Not tested | Not tested |
| 2-2 | 0.250 | 1.167 | 0.213 | Not tested | Not tested |
| 2-3 | 0.222 | 0.685 | 0.141 | Not tested | Not tested |
| 2-4 | 0.776 | 0.970 | 0.353 | Not tested | Not tested |
| 5-1 | Not tested | Not tested | 0.178 | 0.28 | 0.979 |
| 5-2 | Not tested | Not tested | 0.146 | 1.714 | 1.548 |
| 5-3 | Not tested | Not tested | 0.13 | 1.479 | 1.773 |
| 5-4 | Not tested | Not tested | 0.128 | 1.915 | 1.464 |

Group 2 mice #1 and #4, and Group 5 mice #2 and #3 were selected for hybridoma fusions. The animals were sacrificed, the lymph nods and spleens harvested, then B cell hybridoma fusions using P3 mouse myeloma cell line as a fusion partner were generated using standard methods. Fusions were plated and incubated for 11-14 days before screening.

In the first round of screening, hybridomas from group 2 and 5 mice were analyzed by ELISA in 96 well plates, essentially as described above, using the corresponding screening peptides, 2-0 and 5-0. Following several rounds of screening, 48 positive hybridoma lines were identified and transferred to 24 well plates for expansion and additional characterization including epitope mapping. Of the 48 positive lines, 33 were derived from the Group 2 animals that received the MAP2 immunogen while the remaining 15 originated from the Group 5 animals. Most of the hybridoma lines (~94%) were the fusion products of B cells harvested from the spleen. Thirteen of the 48 hybridoma lines expressed IgG, 25 expressed IgM, and the remaining 10 hybridoma lines were expressing both IgG and IgM or were not expressing either IgG or IgM and were therefore expressing either IgA or IgE.

In the second round of screening, hybridomas selected for expansion were re-tested against the relevant screening peptide (either peptide 2-0 or peptide 5-0). 13 of the 48 hybridomas characterized after the 24 well expansion phase exhibited sequence specific binding to the screening peptide 2-0. Other hybridomas bound non-specifically (i.e., bound a variety of oligopeptide sequences), failed to bind (reflecting either a false positive or clonal instability and loss during the transfer and subsequent propagation in 24 well plates) or bound control wells containing BSA.

The 13 hybridomas that specifically bound to screening peptide 2-0 were epitope mapped using ELISA as described above, using 3 different sets of 10mer C-terminal biotinylated mapping peptides: peptides 1-1 to 1-5; 2-1 to 2-9; and 3-1 to 3-9 (see Table 6). 10 of the 12 hybridoma lines exhibited maximum reactivity with a single mapping peptide, 2-1, and that hybridomas 2.03 and 2.11 showed strong binding to different overlapping sets of mapping peptides, peptides 2-1 through 2-3 and 2-7 through 2-9. Because these data showed strong reactivity to a single mapping peptide for most hybridoma lines, we considered the possibility that steric hindrance associated with immobilization of the mapping peptides (specifically, biotin-avidin immobilization) was preventing antibody binding to the epitope present within a cognate series of 10mers, thus potentially biasing the ELISA epitope map results. Thus, we evaluated epitope specificity using a competitive binding assay.

Individual mapping peptides were evaluated for their ability to inhibit antibody binding to the 2-0 screening peptide affixed to streptavidin-coated 96 well plates. In this format, the 10mer mapping peptides were not tethered within the binding pocket of streptavidin and consequently should not be sterically hindered from interacting with a reactive antibody present within the set of 13 hybridomas. Inhibition experiments were performed using standard methods using the 2-0 screening peptide was affixed to streptavidin-coated 96 well plates and 10mer mapping peptide was added to each well.

Using the competitive binding assay, the epitopes recognized by 10 of the 13 hybridomas were determined. Eight of the hybridomas were specific for the epitope PEDTG, hybridoma 2.03 was specific for epitope DTG and hybridoma 2.11 recognized the epitope KTTN. Hybridomas 2.31, 1.02 and 2.12 showed poor discrimination in the competitive inhibition assay. The results of this analysis are summarized in Table 8.

TABLE 8

Epitopes Predicted by Competitive Inhibition

Pattern of 1.01, 2.01, 2.04, 2.06, 2.07 2.08, 2.10 and 2.23: PEDTG

| P1-1 | HSLFHPEDTG |
|---|---|
| P1-2 | SLFHPEDTGQ |
| P1-5 | HPEDTGQVKK |
| P2-1 | PEDTGQVKKT |

2.03 Pattern: DTG

| P1-1 | HSLFHPEDTG |
|---|---|
| P1-2 | SLFHPEDTGQ |
| P1-3 | LFHPEDTGQV |
| P1-4 | FHPEDTGQVK |
| P1-5 | HPEDTGQVKK |
| P2-1 | PEDTGQVKKT |

TABLE 8-continued

Epitopes Predicted by Competitive Inhibition

| | |
|---|---|
| P2-2 | EDTGQVKKTT |
| P2-3 | DTGQVKKTTN |
| 2.11 Pattern: KKTTN | |
| P1-4 | FHPEDTGQVK ??? |
| P2-3 | DTGQVKKTTN |
| P2-4 | TGQVKKTTNV |
| P2-5 | GQVKKTTNVH |
| P2-6 | QVKKTTNVHS |
| P2-7 | VKKTTNVHSL |
| P2-8 | |
| P2-9 | |
| P3-1 | LTPKKTTNVL |
| P3-2 | TPKKTTNVLT |
| P3-3 | PKKTTNVLTV |
| P3-4 | KKTTNVLTVP |
| 2.31 Pattern: A mixture of two clones? | |
| P1-1 | HSLFHPEDTG |
| P1-2 | SLFHPEDTGQ |
| P1-5 | HPEDTGQVKK |
| P2-1 | PEDTGQVKKT |
| P2-7 | VKKTTNVHSL |
| P2-8 | KKTTNVHSLF |
| P2-9 | KTTNVHSLFH |
| P3-2 | TPKKTTNVLT |
| P3-3 | PKKTTNVLTV |
| 1.02 and 2.12 Pattern: Pattern is unclear | |

Although the foregoing invention has been described in some detail by way of illustration and example for purposes of clarity of understanding, the descriptions and exmples should not be construed as limiting the scope of the invention.

What is claimed is:

1. A set of digital antibodies, wherein the set comprises at least about 15 digital antibodies, wherein each of the 15 digital antibodies has been characterized to bind specifically to a different epitope consisting of 3 or 4 or 5 consecutive amino acids, and wherein each digital antibody recognizes a plurality of distinct and different proteins that comprise the same epitope to which the digital antibody binds.

2. The set of digital antibodies according to claim 1, wherein the set comprises 100 digital antibodies that bind epitopes consisting of 3 consecutive amino acids.

3. The set of digital antibodies according to claim 2, wherein the set further comprises 100 digital antibodies that bind epitopes consisting of 4 consecutive amino acids.

4. The set of digital antibodies according to claim 3, wherein the set further comprises 100 digital antibodies that bind epitopes consisting of 5 consecutive amino acids.

5. The set of digital antibodies according to claim 1, wherein the set comprises at least about 20, 30, 40, 50, 60, 70, 80, 90, 100, 200, 300, 400, 500, 600, 700 800, 900, or 1000 digital antibodies.

6. The set of digital antibodies according to claim 1, wherein the set comprises at least 1000 digital antibodies that bind epitopes consisting of 4 consecutive amino acids.

7. The set of digital antibodies according to claim 6, wherein the set further comprises at least 100 digital antibodies that bind epitopes consisting of 5 consecutive amino acids.

8. The set of digital antibodies according to claim 7, wherein the set further comprises at least 100 digital antibodies that bind epitopes consisting of 3 consecutive amino acids.

9. The set of digital antibodies according to claim 1, wherein the digital antibodies are immobilized on a surface.

10. The set of digital antibodies according to claim 4, wherein the digital antibodies are immobilized on a surface.

11. The set of digital antibodies according to claim 9 or 10, wherein the surface is an array.

12. A method for generating a protein binding profile of a sample comprising a plurality of different proteins, said method comprising:
(a) contacting said sample with a set of digital antibodies, under conditions that permit binding, wherein the set of digital antibodies comprises at least about 15 digital antibodies, wherein each of the 15 digital antibodies has been characterized to bind specifically to a different epitope consisting of 3 or 4 or 5 consecutive amino acids, and each digital antibody recognizes a plurality of distinct and different proteins that comprise the same epitope to which the digital antibody binds;
(b) optionally removing an unbound protein; and
(c) detecting binding of protein to said digital antibodies, whereby a protein binding profile of the sample is generated.

13. The method of claim 12, wherein the method further comprises the step of treating the sample with a protein cleaving agent prior to step (a) of contacting the sample with the set of digital antibodies under conditions that permit binding.

14. A method for generating a library of protein binding profiles for two or more different samples each of which comprises a plurality of proteins, said method comprising:
(a) contacting a sample with a set of digital antibodies under conditions that permit binding, wherein the set of digital antibodies comprises at least about 15 digital antibodies, wherein each of the 15 digital antibodies has been characterized to bind specifically to a different epitope consisting of 3 or 4 or 5 consecutive amino acids, and each digital antibody recognizes a plurality of distinct and different proteins that comprise the same epitope to which the digital antibody binds;
(b) optionally removing an unbound protein;
(c) generating a protein binding profile of the sample being tested by detecting binding of protein to the digital antibodies, whereby a protein binding profile is generated; and
(d) repeating steps (a) through (c) with at least two samples.

15. The method of claim 14, wherein the method further comprises the step of treating the sample with a protein cleaving agent prior to step (a) of contacting the sample with the set of digital antibodies under conditions that permit binding.

16. A library of protein binding profiles, wherein the library is prepared using the method of claim 14.

17. A method for characterizing a test sample, comprising:
   (a) contacting the test sample with a set of digital antibodies under conditions that permit binding, wherein the set of digital antibodies comprises at least about 15 digital antibodies, wherein each of the 15 digital antibodies has been characterized to bind specifically to a different epitope consisting of 3 or 4 or 5 consecutive amino acids, and each digital antibody recognizes a plurality of distinct and different proteins that comprise the same epitope to which the digital antibody binds;
   (b) optionally removing an unbound protein;
   (c) generating a protein binding profile of said test sample by detecting binding of protein to the digital antibodies; and
   (d) comparing the generated protein binding profile of the test sample with a protein binding profile of a reference sample to characterize the test sample.

18. A method for determining presence or absence of a bacteria, virus, or cell in a test sample, said method comprising
   (a) contacting the test sample with a set of digital antibodies under conditions that permit binding, wherein the set of digital antibodies comprises at least about 15 digital antibodies, wherein each of the 15 digital antibodies has been characterized to bind specifically to a different epitope consisting of 3 or 4 or 5 consecutive amino acids, and each digital antibody recognizes a plurality of distinct and different proteins that comprise the same epitope to which the digital antibody binds;
   (b) optionally removing an unbound protein;
   (c) generating a protein binding profile of the test sample by detecting binding of protein to the digital antibodies, whereby a protein binding profile is generated; and
   (d) comparing the protein binding profile of the test sample with a protein binding profile of a reference sample, whereby presence or absence of the bacteria, virus or cell in the test sample is determined by the comparison.

19. A method for identifying a test protein in a sample, said method comprising
   (a) contacting a sample comprising or suspected of comprising the test protein with a set of digital antibodies that comprises at least about 15 digital antibodies, wherein each of the 15 digital antibodies has been characterized to bind specifically to a different epitope consisting of 3 or 4 or 5 consecutive amino acids, and each digital antibody recognizes a plurality of distinct and different proteins that comprise the same epitope to which the digital antibody binds; and
   (b) determining the identity of the test protein by detecting of binding of the test protein to the set of digital antibodies, wherein at least about six digital antibodies bind the test protein; and wherein presence of binding indicates presence of at least about six epitopes in the test protein, wherein the identity of the at least about six epitopes is used to identify the test protein.

* * * * *